United States Patent [19]

Zimmerman

[11] 4,337,341
[45] Jun. 29, 1982

[54] 4A-ARYL-OCTAHYDRO-1H-2-PYRINDINES

[75] Inventor: Dennis M. Zimmerman, Mooresville, Ind.

[73] Assignee: Eli Lilly and Company, Indianapolis, Ind.

[21] Appl. No.: 230,556

[22] Filed: Feb. 2, 1981

Related U.S. Application Data

[63] Continuation of Ser. No. 164,994, Jul. 1, 1980, abandoned, which is a continuation of Ser. No. 13,996, Feb. 22, 1979, abandoned, which is a continuation of Ser. No. 864,899, Dec. 27, 1977, abandoned, which is a continuation-in-part of Ser. No. 737,958, Nov. 2, 1976, abandoned.

[51] Int. Cl.³ .................. C07D 221/04; C07D 405/06
[52] U.S. Cl. .................................. 546/112; 260/345.3; 542/400; 542/439; 542/455; 542/469; 546/183; 549/232
[58] Field of Search ................ 546/112; 542/400, 439, 542/455, 469

[56] References Cited

U.S. PATENT DOCUMENTS

| | | | |
|---|---|---|---|
| 3,679,686 | 7/1972 | Hermans et al. | 424/258 X |
| 3,843,666 | 10/1974 | Coombs et al. | 260/310 R X |
| 3,992,387 | 11/1976 | Sturm et al. | 546/23 |
| 4,001,247 | 1/1977 | Zimmerman et al. | 424/258 X |
| 4,001,248 | 1/1977 | Zimmerman et al. | 424/258 X |

FOREIGN PATENT DOCUMENTS 802557  7/1973  Belgium .

OTHER PUBLICATIONS

Boekelheide, V., et al., *J. Am. Chem. Soc.*, 72, 712–715, (1950).

*Primary Examiner*—Richard A. Schwartz
*Attorney, Agent, or Firm*—Karen B. O'Connor; Charles W. Ashbrook; Arthur R. Whale

[57] ABSTRACT

4a-phenyl and substituted phenyl 2,3,4,4a,5,6,7,7a-octahydro-1H-2-pyrindines having a 2-substituent are disclosed. Such compounds are useful as analgesic agents having mixed agonist and antagonist properties. The compounds can be prepared by reacting an amine with a 4-aryl-2,6-dioxocyclopenta[c]pyran, followed by reduction, or alternatively by alkylating a 4a-aryl-octahydro-1H-2-pyrindine at the 2-position.

5 Claims, No Drawings

4A-ARYL-OCTAHYDRO-1H-2-PYRINDINES

CROSS REFERENCE TO RELATED APPLICATION

This application is a continuation of application Ser. No. 164,994, filed July 1, 1980, now abandoned, which is a continuation of application Ser. No. 13,996, filed Feb. 22, 1979, now abandoned, which was a continuation of Ser. No. 864,899, filed Dec. 27, 1977, now abandoned, which was a continuation-in-part of application Ser. No. 737,958, filed Nov. 2, 1976, now abandoned.

BACKGROUND OF THE INVENTION

In recent years, much effort has been devoted to the synthesis of drugs, i.e. analgesics, capable of relieving the sensation of pain. Several of the currently available analgesics are limited in their use due to various undesirable side effects which frequently accompany their continued use. Such side effects include addiction and allergy. Illustrative of new analgesic drugs which have recently been discovered are the decahydroisoquinolines, particularly the 4a-aryl-trans-decahydroisoquinolines which are described in Belgium Pat. No. 802,557.

The present invention relates to a group of 4a-aryl-2-substituted-octahydro-1H-2-pyrindines. Such compounds are somewhat structurally related to the aforementioned isoquinoline derivatives; however, the compounds provided by this invention have not heretofore been synthetically available. Only simple unsubstituted pyridine analogs are known in the literature. Volodina et al., for example, prepared certain octahydro-2-pyridines, none of which were substituted at the 4a-position; *Dokl. Akad. Nauk USSR* 173(2), 342–5(1967) cf. C.A. Vol. 67, 6034(1967). Similarly, Prochazka et al. prepared a trans-octahydro-2-pyrindine lacking a 4a-substituent, *Coll. Czech. Chem. Commun.*, 31(9), 3824–8(1966), Cf. C.A. Vol. 65, 13651(1966).

An object of this invention is to provide 4a-phenyl and substituted phenyl 2,3,4,4a,5,6,7,7a-octahydro-1H-2-pyridines not heretofore known or available, and intermediates useful in their preparation.

SUMMARY OF THE INVENTION

This invention relates to new bicylic compounds characterized as being octahydro-1H-2-pyrindines, alternatively referred to as hexahydro-1H-cyclopenta[c]pyridines. Specifically, the invention provides 4a-aryl-2-substituted-2,3,4,4a,5,6,7,7a-octahydro-1H-2-pyrindines of the general formula

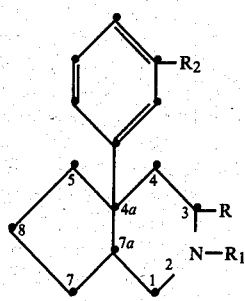

wherein: R is hydrogen or $C_1$-$C_5$ alkyl; $R_1$ is hydrogen, $C_1$-$C_8$ alkyl, $CH_2R_3$, or

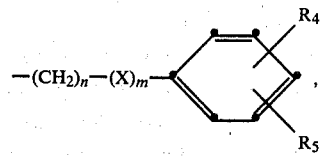

in which $R_3$ is $C_2$-$C_7$ alkenyl, $C_3$-$C_6$ cycloalkyl, furyl, or tetrahydrofuryl; $R_4$ and $R_5$ independently are hydrogen, $C_1$-$C_3$ alkyl, or halogen; n is 0, 1, 2 or 3; m is 0 or 1, except that when m is 0, n is other than 0; X is CO, CHOH, CH=CH, S, or O, except that when n is O, X is other than S or O; and $R_2$ is hydrogen, hydroxy, $C_1$-$C_3$ alkoxy, or $C_1$-$C_3$ alkanoyloxy. Considered within the scope of this invention are the nontoxic pharmaceutically acceptable acid addition salts of the pyrindine bases having the above formula. Additionally encompassed within the scope of this invention are intermediate compounds having the above formula wherein $R_1$ is

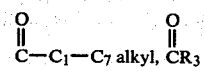

in which $R_3$ has the above defined meaning,

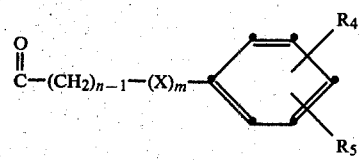

in which n, m, X, $R_4$ and $R_5$ have the above defined meaning.

A preferred group of octahydropyrindines comprehended by the invention are those having the above formula wherein R is hydrogen. A more preferred group of compounds have the above formula wherein R is hydrogen and $R_1$ is $C_1$-$C_8$ alkyl or $CH_2R_3$ in which $R_3$ is $C_2$-$C_7$ alkenyl or $C_3$-$C_6$ cycloalkyl. The most preferred compounds within this latter preferred group are those of the above formula wherein $R_2$ is hydroxy or $C_1$-$C_3$ alkoxy, particularly methoxy. An especially preferred group of intermediate compounds have the above formula wherein $R_1$ is hydrogen.

DETAILED DESCRIPTION OF THE INVENTION

As used throughout the present specification and in the appended claims, the term "$C_1$-$C_8$ alkyl" refers to both straight and branched chains of eight carbon atoms or less. Examples of typical $C_1$-$C_8$ alkyl groups include methyl, ethyl, propyl, butyl, iropropyl, isobutyl, pentyl, 3-methylpentyl, 1,2-dimethylpentyl, 2-methylbutyl, 3-ethylpentyl, n-octyl, 2-methylheptyl, isoheptyl, 3-ethylhexyl, 1,3,3-trimethylpentyl, and related groups.

The term "$CH_2R_3$, in which $R_3$ is $C_2$-$C_7$ alkenyl" refers to both straight and branched alkenyl groups having eight or less carbon atoms, including groups such as allyl, 3-butenyl, 2-pentenyl, 3-pentenyl, 2-methyl-2-butenyl, 3-methyl-3-pentenyl, 3-isohexenyl, 2-ethyl-3-butenyl, 4-hexenyl, 3-methyl-2-pentenyl, 3-octenyl, 2-isooctenyl, 2-isopropyl-3-butenyl, 2,3-dimethyl-2- butenyl, 5-heptenyl, 6-octenyl, 2-methyl-3-heptenyl, and related alkenyl groups.

Additionally included within the definition of $R_1$ in the above formula is the group represented by $CH_2R_3$ in which $R_3$ is $C_3$-$C_6$ cycloalkyl. Such groups include cyclopropylmethyl, cyclobutylmethyl, cyclopentylmethyl and cyclohexylmethyl. $R_1$ can also represent groups such as 2-tetrahydrofurylmethyl, 3-tetrahydrofurylmethyl, and 3-furylmethyl.

In the above formula, $R_1$ can also be a group of the formula

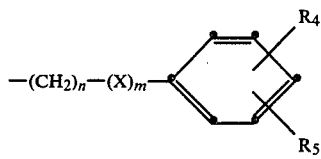

in which n is 0, 1, 2, or 3, m is 0 or 1, except that when m is 0, n is other than 0; X is CO, CHOH, CH=CH, S or O, except that when n is O, X is other than S or O; and $R_4$ and $R_5$ independently are hydrogen, $C_1$-$C_3$ alkyl, or halogen. In such formula, the term "$C_1$-$C_3$ alkyl" includes methyl, ethyl and propyl. "Halogen" refers to fluorine, chlorine, bromine and iodine. Examples of typical $R_1$ groups represented by the above formula include benzyl, 2-phenylethyl, 3-phenylpropyl, 3-methylbenzyl, 4-chlorobenzyl, 2,4-dibromobenzyl, 2-(2-methyl-5-ethylphenyl)ethyl, 3-(4-isopropylphenyl)propyl, benzoylmethyl, benzoylethyl, 4-iodobenzoylmethyl, 2-methyl-4-chlorobenzoylmethyl, 2-phenyl-2-hydroxyethyl, 3-phenyl-3-hydroxypropyl, 2-(4-fluorophenyl)-2-hydroxyethyl, phenoxymethyl, 3,5-diethylphenoxymethyl, 3-phenylthiopropyl, 2-methylphenylthiomethyl, 3,5-dichlorophenylthiomethyl, 3-chloro-5-bromophenylthiomethyl, and related groups.

In accordance with this invention, the foregoing pyrindine derivatives having the above formula wherein R is hydrogen are produced by first reacting an amine, specifically ammonia or a primary amine, with a cyclic anhydride, namely a 4a-aryl-tetrahydro-2,6-dioxocyclopenta[c]pyran, according to the following generalized reaction scheme:

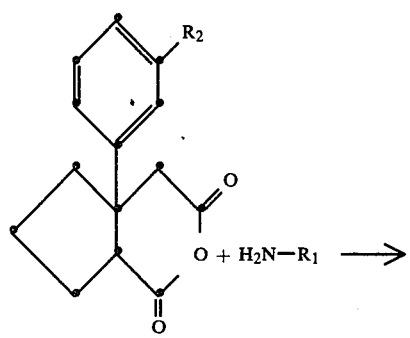

-continued

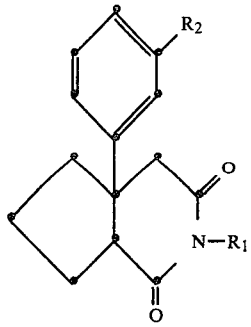

in which $R_1$ and $R_2$ have the above-defined meanings. The 1,3-dioxo-4a-aryl-2,3,4,4a,5,6,7,7a-octahydro-1H-2-pyrindine, a cyclic imide, so produced is then reduced at the 1 and the 3-oxo groups to provide a pyrindine derivative of the invention. In practice, it is preferred to utilize 4a-aryl-tetrahydro-2,6-dioxocyclopenta[c]pyrans in which the substituent on the aryl group, defined in the above formulas by $R_2$, is selected from hydrogen and $C_1$-$C_3$ alkoxy groups. Among such $C_1$-$C_3$ alkoxy groups, the methoxy group is preferred since such group is readily de-methylated at a later stage to provide a hydroxyl moiety, as will be described hereinafter. In the reaction of an amine with the above-noted cyclic anhydride, it is similarly preferred to utilize amines such as ammonia, $C_1$-$C_8$ alkyl amines, especially methylamine, as well as aryl amines, particularly benzyl amine. The 2-methyl and 2-benzyl pyrindine derivatives so produced are readily converted to the corresponding 2-unsubstituted pyrindine, which compound is easily derivatized by alkylation and acylation to produce other 2-substituted compounds of the invention. Such conversions will be elaborated upon hereinbelow.

In the preparation of the 1,3-dioxo-4a-aryl-2,3,4,4a,5,6,7,7a-octahydro-1H-2-pyrindines according to the above-noted reaction scheme, the 4-aryl-tetrahydro-2,6-dioxo-cyclopenta[c]pyran and the amine are typically combined in approximately equimolar quantities, although an excess of either reactant can be used if desired. The reaction can be carried out in any of a number of commonly used unreactive organic solvents, including aromatic solvents such as benzene, toluene, xylene, methoxybenzene, and nitrobenzene, as well as non-aromatic solvents such as chloroform, dichloromethane, dimethyl sulfoxide, nitromethane, acetone, tetrahydrofuran, dimethylformamide, dioxane, and the like. The reaction typically is conducted at an elevated temperature, for instance at a temperature ranging from about 50° C. to about 200° C., preferably at a temperature of about 80° C. to about 150° C. Since the reaction between the amine and the cyclic anhydride to form the corresponding cyclic imide is accompanied by the formation of water, it may be desirable to conduct the reaction in such a way that water is removed from the reaction mixture as it is formed. Any of the commonly used techniques for maintaining a dry reaction mixture can be utilized, including the use of molecular seives, or alternatively a Dean Stark trap can be employed with reaction solvents such as benzene and toluene. The reaction between the amine and the cyclic anhydride normally is substantially complete within 24 to 72 hours; however, longer reaction times apparently are not detrimental to the product being formed and can be incorporated if desired. The cyclic imide thus formed, namely the 4a-aryl-2,3,4,4a,5,6,7,7a-octahydro-1,3-dioxo-1H-2-pyrindine, is readily isolated by removal of the reaction solvent, for instance by evaporation under reduced pressure, and the product can be further purified by standard procedures such as acid and base extraction, crystallization, chromatography, and the like.

As hereinbefore stated, the 4-aryl-tetrahydro-2,6-dioxocyclopenta[c]pyran can be reacted with ammonia to provide the corresponding 4a-aryl-2,3,4,4a,5,6,7,7a-octahydro-1,3-dioxo-1H-2-pyrindine which is unsubstituted at the 2-position, or alternatively the pyran derivative can be reacted with a primary amine to provide directly a 4a-aryl-2-substituted-2,3,4,4a,5,6,7,7a-octahydro-1,3-dioxo-1H-2-pyrindine. It was further pointed out that when it is desired to react the pyran derivative with a primary amine so as to obtain a 2-substituted pyrindine derivative, it is preferred that such primary amine be methyl amine or benzyl amine. Such primary amines are preferred because they provide, when reacted with a 4-aryl-tetrahydro-2,6-dioxocyclopenta[c]pyran, a 2-substituted 1,3-dioxo-pyrindine derivative which, when reduced, affords a 2-substituted pyrindine derivative in which the 2-substituent can be readily removed to afford a 2-unsubstituted pyrindine derivative. The 2-unsubstituted pyrindine derivative is an extremely important intermediate in the preparation of all of the pyrindines of this invention, as will be described hereinbelow. It should be noted, however, that while the preferred primary amines for reacting with the aforementioned pyran derivative are methyl amine and benzyl amine, essentially any primary amine can be reacted with the pyran derivative to provide the corresponding 4a-aryl-2-substituted-2,3,4,4a,5,6,7,7a-octahydro-1,3-dioxo-1H-2-pyrindine. It will be further noted that since the latter named compound is a 1,3-dioxopyrindine derivative, that such compound must undergo a reduction of the 1- and the 3-oxo groups to provide the pharmacologically useful pyrindine of this invention. It is preferred, therefore, that any group attached at the 2-position of such 4a-aryl-2-substituted-2,3,4,4a,5,6,7,7a-octahydro-1,3-dioxo-1H-2-pyrindine be a group which is substantially resistant to the reduction procedures utilized to reduce the 1- and the 3-oxo groups. For groups which are not so resistant to reduction, it is preferred to introduce such groups by alkylation, or acylation and subsequent reduction, of the 2-unsubstituted pyrindine derivatives.

The following list presents representative 4a-aryl-2,3,4,4a,5,6,7,7a-octahydro-1,3-dioxo-1H-2-pyrindines which are routinely prepared directly by reaction of an amine with a cyclic anhydride as hereinabove described and which are subsequently reduced to provide pharmacologically useful pyrindine derivatives as will be described in detail hereinbelow.

4a-phenyl-2,3,4,4a,5,6,7,7a-octahydro-1,3-dioxo-1H-2-pyrindine;
4a-phenyl-2-methyl-2,3,4,4a,5,6,7,7a-octahydro-1,3-dioxo-1H-2-pyrindine;
4a-(3-methoxyphenyl)-2-n-pentyl-2,3,4,4a,5,6,7,7a-octahydro-1,3-dioxo-1H-2-pyrindine;
4a-(3-ethoxyphenyl)-2-(3-phenylpropyl)-2,3,4,4a,5,6,7,7a-octahydro-1,3-dioxo-1H-2-pyrindine;
4a-phenyl-2-phenylmethyl-2,3,4,4a,5,6,7,7a-octahydro-1,3-dioxo-1H-2-pyrindine;
4a-(3-propoxyphenyl)-2-n-propyl-2,3,4,4a,5,6,7,7a-octahydro-1,3-dioxo-1H-2-pyrindine;
4a-(3-methoxyphenyl)-2-(2-tetrahydrofurylmethyl)-2,3,4,4a,5,6,7,7a-octahydro-1,3-dioxo-1H-2-pyrindine;
4a-phenyl-2-[2-(3-chlorophenyl)ethyl]-2,3,4,4a,5,6,7,7a-octahydro-1,3-dioxo-1H-2-pyrindine;
4a-(3-methoxyphenyl)-2-cyclopropylmethyl-2,3,4,4a,5,6,7,7a-octahydro-1,3-dioxo-1H-2-pyrindine;
4a-(3-methoxyphenyl)-2-phenylmethyl-2,3,4,4a,5,6,7,7a-octahydro-1,3-dioxo-1H-2-pyrindine;
4a-(3-methoxyphenyl)-2,3,4,4a,5,6,7,7a-octahydro-1,3-dioxo-1H-2-pyrindine;
4a-phenyl-2-(3,4-dimethylphenyl)methyl-2,3,4,4a,5,6,7,7a-octahydro-1,3-dioxo-1H-2-pyrindine;
4a-(3-propoxyphenyl)-2-(4-phenylbutyl)-2,3,4,4a,5,6,7,7a-octahydro-1,3-dioxo-1H-2-pyrindine, and the like.

As has already been pointed out, the aforementioned 4a-aryl-2,3,4,4a,5,6,7,7a-octahydro-1,3-dioxo-1H-2-pyrindines are converted to the 4a-aryl-2,3,4,4a,5,6,7,7a-octahydro-1H-2-pyrindines of this invention by reduction of the 1-oxo group and the 3-oxo group. Such reduction be be accomplished by any of a number of common reduction procedures familiar to those skilled in the art. For instance, the 1,3-dioxo-pyrindine derivative can be reacted with any of a number of alkali metal hydride reducing agents, including lithium aluminum hydride, sodium borohydride, lithium tritert.-butoxy aluminum hydride, and lithium trimethoxy aluminum hydride. Reducing agents such as zinc and acetic acid and catalytic hydrogenation can also be utilized if desired. The preferred process for reducing a 4a-aryl-2,3,4,4a,5,6,7,7a-octahydro-1,3-dioxo-1H-2-pyrindine involves the use of lithium aluminum hydride as the reducing agent. Typically a 4a-aryl-2,3,4,4a,5,6,7,7a-octahydro-1,3-dioxo-1H-2-pyrindine, such as 4a-phenyl-2-methyl-2,3,4,4a,5,6,7,7a-octahydro-1,3-dioxo-1H-2-pyrindine for instance, is commingled with about a two molar quantity of lithium aluminum hydride in an unreactive organic solvent. Unreactive organic solvents commonly used in the reaction include tetrahydrofuran, diethyl ether, dioxane, diglyme, and related solvents. The reaction normally is carried out at a temperature ranging from about 20° C. to about 100° C., and when carried out at such temperature, the reaction routinely is substantially complete after about 4 to 20 hours. The product normally is recovered by first decomposing any unreacted reducing agent which may remain in the reaction mixture. Such decomposition is accomplished, in the case where lithium aluminum hydride is the reducing agent for instance, by adding to the reaction mixture an ester which readily reacts with any excess reducing agent. An ester such as ethyl acetate is commonly utilized for such purpose. Following the addition of the ester to the reaction mixture, an aqueous solution of ammonium chloride typically is added to the reaction mixture in order to coagulate any inorganic salts formed in the reaction, and then the product is extracted therefrom into a suitable organic solvent, such as ethyl acetate or tetrahydrofuran. The organic extracts are then combined and concentrated by evaporation of the solvent, thus providing the reduced product, namely a 4a-aryl-2,3,4,4a,5,6,7,7a-octahydro-1H-2-pyrindine. Such product typically exists as an oil and is conveniently further purified if desired by methods such as distillation and chromatography, or alternatively such compound can be converted to an acid addition salt which can then be purified by crystallization.

Compounds of this invention which are thus readily provided by reducing the 1-oxo and the 3-oxo groups of a 4a-aryl-2,3,4,4a,5,6,7,7a-octahydro-1,3-dioxo-1H-2-pyrindine according to the above-described procedures include, among others:

4a-phenyl-2,3,4,4a,5,6,7,7a-octahydro-1H-2-pyrindine;
4a-(3-methoxyphenyl)-2,3,4,4a,5,6,7,7a-octahydro-1H-2-pyrindine;
4a-(3-ethoxyphenyl)-2-methyl-2,3,4,4a,5,6,7,7a-octahydro-1H-2-pyrindine;
4a-phenyl-2-ethyl-2,3,4,4a,5,6,7,7a-octahydro-1H-2-pyrindine;
4a-(3-isopropoxyphenyl)-2-benzyl-2,3,4,4a,5,6,7,7a-octahydro-1H-2-pyrindine;
4a-phenyl-2-isobutyl-2,3,4,4a,5,6,7,7a-octahydro-1H-2-pyrindine;
4a-(3-methoxyphenyl)-2-(4-ethylhexyl)-2,3,4,4a,5,6,7,7a-octahydro-1H-2-pyrindine;
4a-(3-ethoxyphenyl)-2-(3-chlorobenzyl)-2,3,4,4a,5,6,7,7a-octahydro-1H-2-pyrindine; and the like.

This invention additionally comprehends 4a-aryl-octahydro-1H-2-pyrindines which bear an alkyl substituent at the 3-position. Such compounds have the above formula wherein R is $C_1$–$C_5$ alkyl, such as methyl, ethyl, isopropyl, butyl and pentyl, and are prepared by cyclization of 1-aminomethyl (or substituted aminomethyl)-2-aryl-2-alkenyl cyclopentane, as depicted by the following generalllized reaction scheme:

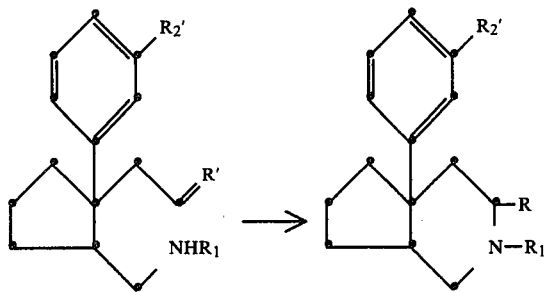

in which R' is $C_1$–$C_5$ alkylidene, for instance methylidene, ethylidene and isopropylidene; $R_1$ is as above defined, and $R_2'$ is hydrogen or alkoxy. Such cyclization of an aminomethyl alkenyl cyclopentane derivative is accomplished by reaction of such compound with mercuric chloride and a reducing agent such as sodium borohydride. For example, a compound such as 1-(N-ethyl)aminomethyl-2-(3-ethoxyphenyl)-2-(3-methyl-2-butenyl)cyclopentane can be reacted with preferably about an equimolar quantity of mercuric chloride in an unreactive solvent such as diethyl ether, tetrahydrofuran, dioxane, or the like. It is not required that equimolar quantities of the reactants be utilized, and an excess of either can be incorporated if desired. Reaction of mercuric chloride with the 1-aminomethyl-2-aryl-2-alkenylcyclopentane derivative forms a mercurial chloride complex at the 2-alkenyl moiety, which complex is preferably not isolated but is reduced, thereby effecting cyclization to provide the corresponding 3-alkyl pyridine derivative of the invention. Reduction of the aforementioned mercurial chloride complex is readily accomplished by reaction with about an equimolar quantity of a reducing agent such as sodium borohydride. Such reductions are generally carried out in an unreactive solvent such as diethyl ether or tetrahydrofuran. The reduction reaction is routinely carried out at a temperature of about 25° C., and usually is complete within about one-half to three hours. The product, a 3-alkyl pyridine derivative having the above formula wherein R is $C_1$–$C_5$ alkyl, is isolated by simply washing the reaction mixture with water and then removing the reaction solvent. The 3-alkyl pyridine derivative so formed normally needs no further purification, but if desired can be distilled, crystallized, or converted to an acid addition salt which generally can be crystallized. Typical 3-alkyl-octahydropyrindine derivatives routinely prepared as above described include the following:

4a-phenyl-2,3-dimethyl-2,3,4,4a,5,6,7,7a-octahydro-1H-2-pyrindine;
4a-(3-methoxyphenyl)-2-ethyl-3-pentyl-2,3,4,4a,5,6,7,,7a-octahydro-1H-2-pyrindine;
4a-(3-isopropoxyphenyl)-2-benzyl-3-isopropyl-2,3,4,4a,5,6,7,7a-octahydro-1H-2-pyrindine; and
4a-phenyl-3-methyl-2,3,4,4a,5,6,7,7a-octahydro-1H-2-pyrindine.

As was hereinbefore noted, very important intermediates for preparing all of the pyridine derivatives of this invention are the 2-unsubstituted pyridine derivatives, those in which $R_1$ in the above formula is hydrogen. Such compounds can be easily alkylated or acylated at the 2-position to provide pharmacologically active octahydropyrindines of the invention, or in the case of the N-acylated derivatives, to provide intermediates which are easily converted to the active analgesics of the invention. It is therefore often desirable to prepare, according to the above-described processes, 4a-aryl-2-substituted-2,3,4,4a,5,6,7,7a-octahydro-1H-2pyrindines in which the 2-substituent is readily removable so as to provide the corresponding 2-unsubstituted octahydropyrindine derivatives. As previously pointed out, N-methyl and N-benzyl groups are readily cleavable to afford the corresponding 2-unsubstituted pyrindine derivative. The 2-methyl pyrindine derivatives prepared as above described can be reacted with a haloformate ester such as phenyl chloroformate or ethyl chloroformate to afford the corresponding carbamate at the pyrindine 2-position. Such carbamate is then reacted with an aqueous base such as sodium hydroxide to effect cleavage of the 2-carbamate moiety and thus provide the corresponding 2-unsubstituted pyrindine derivative. Such method for the cleavage of an N-methyl group is that of Abel-Monen and Portoghese as described in *J. Med. Chem.*, 15, 208(1972).

Similarly, the aforementioned 4a-aryl-2-benzyl-2,3,4,4a,5,6,7,7a-octahydro-1H-2-pyrindines are readily converted to the corresponding 2-unsubstituted pyrindine derivative by simple debenzylation. Such debenzylation may be achieved by catalytic hydrogention, utilizing for instance a catalyst such as five percent palladium suspended on carbon. Such debenzylation reactions are quite general for preparing secondary amines and are described in detail by Hartung and Simonoff, *Org. Reactions*, 7, 277(1953), and by Loenard and Fuji, *J. Amer. Chem. Soc.*, 85, 3719 (1963).

As can readily be seen from the foregoing discussion, the following representative 2-unsubstituted pyridine derivatives are very important intermediates for the preparation of the pharmacologically active pyridines of this invention.

4a-phenyl-2,3,4,4a,5,6,7,7a-octahydro-1H-2-pyrindine;
4a-(3-methoxyphenyl)-2,3,4,4a,5,6,7,7a-octahydro-1H-2-pyrindine;

4a-(3-ethoxyphenyl)-2,3,4,4a,5,6,7,7a-octahydro-1H-2-pyrindine;

4a-(3-isopropoxyphenyl)-2,3,4,4a,5,6,7,7a-octahydro-1H-2-pyrindine;

4a-phenyl-2methyl-2,3,4,4a,5,6,7,7a-octahydro-1H-2-pyrindine;

4a-phenyl-2-ethyl-2,3,4,4a,5,6,7,7a-octahydro-1H-2-pyrindine;

4a-(3-methoxyphenyl)-2-n-pentyl-2,3,4,4a,5,6,7,7a-octahydro-1H-2-pyrindine, and 4a-(3-methoxyphenyl)-2-isopropyl-2,3,4,4a,5,6,7,7a-octahydro-1H-2-pyrindine.

The 4a-aryl-2-unsubstituted-2,3,4,4a,5,6,7,7a-octahydro-1H-2-pyrindines thus prepared can be alkylated by normal procedures to provide pharmacologically active 2-substituted pyrindine derivatives, or can be acylated to provide intermediates which are readily converted to active analgesic drugs. For example, a 4a-aryl-2,3,4,4a,5,6,7,7a-octahydro-1H-2-pyrindine can be alkylated at the 2-position by reaction with essentially any reactive derivative of an alkyl group. Such alkylating agents are compounds of the formula $R_1$-Z in which $R_1$ is as defined hereinabove and Z is any of a number of groups commonly referred to as good leaving groups. Groups most commonly known as good leaving groups include the halogens, particularly chlorine, bromine and iodine, para-toluenesulfonyl (tosyl), phenylsulfonyl, methanesulfonyl (mesyl), para-bromophenylsulfonyl (brosyl), and azido. It will be noted that when reference is made herein to an alkylating agent having the formula $R_1$-Z, it is intended that the alkyl portion of such alkylating agent can be derivatized, for instance by unsaturated substituents, aryl substituents, cycloalkyl substituents, and the like. The term "alkylating agent having the formula $R_1$-Z" thus includes compounds such as methyl chloride, ethyl bromide, 5-methylheptyltosylate, allyl bromide, 4-hexenyl iodide, 3-ethyl-4-pentenyl brosylate, cyclopropylmethyl chloride, cyclobutylmethyl iodide, cyclohexylmethyl mesylate, 3-tetrahydrofurylmethyl bromide, 2-furylmethyl azide, 2-phenylethyl chloride, 3-benzoylpropyl bromide, 2-(3-chlorophenylthio)ethyl azide, phenoxymethyl bromide, 3-isopropylphenylthiomethyl bromide, and related groups.

In accordance with this invention then, a 4a-aryl-2,3,4,4a,5,6,7,7a-octahydro-1H-2-pyrindine can be reacted with an alkylating agent to provide the corresponding 4a-aryl-2-substituted-2,3,4,4a,5,6,7,7a-octahydro-1H-2-pyrindine. Such alkylation reaction is quite general and can be accomplished by commingling the appropriate 4a-aryl-octahydro-1H-2-pyrindine with the appropriate alkylating agent, preferably in an unreactive organic solvent. The alkylating agent typically is utilized in excess amounts, for instance from about 0.5 to about 2.0 molar excess relative to the pyrindine derivative. Unreactive organic solvents commonly utilized in the reaction include ethers such as diethyl ether, dioxane, tetrahydrofuran, as well as solvents such as benzene, dichloromethane, dimethylformamide, dimethyl sulfoxide, nitromethane, hexamethylphosphortriamide, and the like. A base is preferably incorporated in the alkylation reaction to act as an acid scavenger since the reaction of the pyrindine derivative and the alkylating agent generally is accompanied by the formation of an acid such as hydrochloric acid or para-toluenesulfonic acid which may act to tie up any unreacted 2-pyrindine derivative as a salt. Bases commonly utilized as acid scavengers in such reaction include sodium bicarbonate, potassium carbonate, sodium hydroxide, triethylamine, pyrindine, and the like. Typically, about one equivalent amount of base is employed; however, excessive amounts can be incorporated if desired. The alkylation reaction normally is carried out at an elevated temperature ranging from about 50° C. to 200° C., and at such temperature, the reaction normally is substantially complete within about 1 to 10 hours; however, longer reaction times are not detrimental and can be used if desired. The product typically is recovered by simply adding water to the reaction mixture and then extracting the product therefrom into a water-immiscible organic solvent such as benzene, ethyl acetate, dichloromethane, diethyl ether, chloroform, or related solvents. Upon removal of the solvent from such extracts, for instance by evaporation under reduced pressure, there is obtained the product 4a-aryl-2-substituted-2,3,4,4a,5,6,7,7a-octahydro-1H-2-pyrindine, which compound exists either as an oil or as a solid at room temperature. The product so formed can be further purified if desired by standard procedures including chromatography, crystallization, distillation, or alternatively such pyrindine product can be converted to an acid addition salt by reaction with an inorganic or organic acid. Such salts routinely are highly crystalline solids and are readily recrystallized to provide a solid salt of high purity. If desired such salt can then be treated with a base such as sodium hydroxide or potassium carbonate, thereby cleaving the salt to provide the purified 4a-aryl-2-substituted-2,3,4,4a,5,6,7,7a-octahydro-1H-2-pyrindine as a free base.

As herebefore indicated, the 2-unsubstituted pyrindine derivatives, namely the 4a-aryl-octahydro-1H-2-pyrindines and the 4a-aryl-3-alkyl-octahydro-1H-2-pyrindines, can be converted to a 2-substituted pyrindine derivative which is either a pharmacologically useful agent per se, or one which can be readily converted to a pharmacologically useful agent. For example, reaction of a 4a-aryl-2,3,4,4a,5,6,7,7a-octahydro-1H-2-pyrindine with an alkylating agent such as 2-benzoylethyl iodide provides the corresponding 4a-aryl-2-(2-benzoylethyl)octahydro-2,3,4,4a,5,6,7a-2-pyrindine, and active analgesic. If desired, such compound can be reduced at the benzoyl carbonyl moiety, for instance by reaction with a reducing agent such as lithium aluminum hydride, to afford the corresponding 4a-aryl-2-(3-hydroxy-3-phenyl)propyl-2,3,4,4a,5,6,7,7a-octahydro-1H-2-pyrindine, also a useful analgesic agent. Additionally, a 2-unsubstituted pyrindine derivative can be acylated with any of a number of acylating agents to provide an N-acylated pyrindine derivative, a compound of this invention wherein $R_1$ is

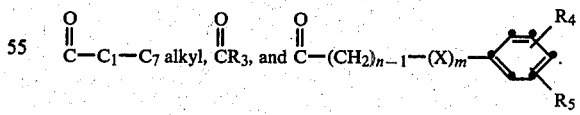

$$\overset{O}{\underset{\|}{C}}-C_1-C_7 \text{ alkyl}, \overset{O}{\underset{\|}{C}}R_3, \text{ and } \overset{O}{\underset{\|}{C}}-(CH_2)_{n-1}-(X)_m-\underset{R_5}{\overset{R_4}{\diagup}}.$$

Such N-acylated pyrindines, upon reduction of the carbonyl moiety, provide 2-substituted pyrindine derivatives of this invention which are active analgesics. For example, a 4a-aryl-3-alkyl-2,3,4,4a,5,6,7,7a-octahydro-1H-2-pyrindine can be acylated with any common acylating agent such as an acid halide or acid anhydride. Examples of commonly used acylating agents include acetyl chloride, pentanoylchloride, 4-hexenoyl chloride, cyclobutylformyl bromide, 2-(tetrahydrofuryl)formyl chloride, benzoyl bromide, phenoxyacetyl iodide, 3,4-dimethylphenylacetyl chloride, 3-(2-fluorophenyl)propionyl chloride, phenylthioacetyl bromide, 4-phenyl-3-butenoyl chloride, acetic anhydride, hexanoic anhydride, and the like. The acylation of the 2-unsubstituted pyridine derivative with an acylating agent such as the aforementioned is carried out by commingling approximately equimolar quantities of the pyridine derivative and the acylating agent in an unreactive organic solvent such as dichloromethane, ethanol, tetrahydrofuran, or the like. The reaction typically utilizes a base such as sodium bicarbonate, potassium carbonate, or propylene oxide to serve as an acid scavenger. The reaction is best carried out at a temperature of about $-20°$ C. to about $30°$ C., and generally is complete within 1 to 8 hours. The product, for example a 4a-aryl-3-alkyl-2-acylated-2,3,4,4a,5,6,7,7a-octahydro-1H-2-pyrindine, is readily isolated by simply removing the reaction solvent by evaporation. The product so formed normally is not purified further, but rather is reduced immediately to provide a 4a-aryl-3-alkyl-2-substituted-2,3,4,4a,5,6,7,7a-octahydro-1H-2-pyrindine of this invention. Such reduction of the N-acyl carbonyl group can be accomplished by reaction of the acylated pyrindine derivative with a reducing agent such as lithium aluminum hydride or by catalytic hydrogenation.

It will additionally be recognized that still other modifications can be made on certain of the 4a-aryl-2-substituted-2,3,4,4a,5,6,7,7a-octahydro-1H-2-pyrindines of this invention. For example, while a 4a-aryl pyridine derivative wherein the aryl group is a 3-hydroxyphenyl moiety can be prepared by starting with a 2-(3-hydroxyphenyl)-2-ethoxycarbonylmethyl-cyclohexanone and modifying such compound according to the various processes discussed hereinabove, it might be preferable to prepare a 4a-(3-methoxyphenyl)-2-substituted-2,3,4,4a,5,6,7,7a-octahydro-1H-2-pyrindine, and then convert the 3-methoxy group of such 4a-aryl substituent to a hydroxy group. Such conversion is readily accomplished by reacting a 4a-(3-methoxyphenyl)-pyrindine derivative with hydrobromic acid in acetic acid. Such reaction is quite general for the conversion of a methoxyphenyl group to a hydroxyphenyl group. The hydroxy group of such 4a-(3-hydroxyphenyl)pyrindines can, if desired, by acylated with common $C_1$-$C_3$ alkanoyl acylating agents, for instance acetyl chloride or propionyl anhydride, thereby providing the corresponding 4a-(3-alkanoyloxyphenyl)pyrindine derivatives.

As hereinbefore pointed out, the 4a-aryl-2-substituted-octahydro-1H-2-pyrindine derivatives of this invention can be reacted with an organic or inorganic acid so as to provide a crystalline salt which can be purified by crystallization, and which then can be converted back to the pyrindine free base by treatment with a suitable base such as sodium hydroxide. Certain of the acid addition salts are encompassed within the scope of this invention. Specifically, there are included herein the non-toxic pharmaceutically acceptable acid addition salts of the pyrindine bases which are described hereinabove. Such non-toxic pharmaceutically acceptable acid addition salts are prepared by reacting a 4a-aryl-2-substituted-octahydro-1H-2-pyrindine of this invention with an organic or an inorganic acid. Acids commonly used to prepare the pharmaceutically acceptable acid addition salts of this invention include the hydrogen halide acids such as hydrogen chloride, hydrogen bromide, and hydrogen iodide, as well as acids such as sulfuric, phosphoric, nitric, perchloric, phosphorous, nitrous, and related acids. Organic acids commonly used to prepare pharmaceutically acceptable acid addition salts of the pyrindines of this invention include acetic, propionic, para-toluenesulfonic, chloroacetic, maleic, tartaric, succinic, oxalic, citric, lactic, palmitic, stearic, benzoic, and related acids. The pharmaceutically acceptable acid addition salts of this invention can be conveniently prepared by simply dissolving a 4a-aryl-2-substituted-octahydro-1H-2-pyrindine in a suitable solvent such as diethyl ether, ethyl acetate, acetone, ethanol, or the like, and adding to such solution either an equivalent amount or an excess of a suitable acid. The salt so formed normally crystallizes out of solution and can be recovered by filtration, and is accordingly ready for use as a pharmacological agent, or can be further purified by recrystallization from common solvents such as acetone and methanol.

The following list of 4a-aryl-2-substituted-2,3,4,4a,5,6,7,7a-octahydro-1H-2-pyrindines is representative of the compounds falling within the scope of this invention.

4a-phenyl-2-(3-ethylpentyl)-2,3,4,4a,5,6,7,7a-octahydro-1H-2-pyrindine;

4a-(3-methoxyphenyl)-2-(n-octyl)-2,3,4,4a,5,6,7,7a-octahydro-1H-2-pyrindinium bromide;

4a-(3-hydroxyphenyl)-2-(2-propenyl)-2,3,4,4a,5,6,7,7a-octahydro-1H-2-pyrindine;

4a-(3-propoxyphenyl)-2-(2,3-dimethyl-4-hexenyl)-2,3,4,4a,5,6,7,7a-octahydro-1H-2-pyrindine;

4a-phenyl-2-(5-heptenyl)-2,3,4,4a,5,6,7,7a-octahydro-1H-2-pyrindinium acetate;

4a-(3-hydroxyphenyl)-2-cyclopentylmethyl-2,3,4,4a,5,6,7,7a-octahydro-1H-2-pyrindinium oxalate;

4a-(3-ethoxyphenyl)-2-(2-tetrahydrofurylmethyl)-2,3,4,4a,5,6,7,7a-octahydro-1H-2-pyrindine;

4a-phenyl-2-(2-phenoxyethyl)-2,3,4,4a,5,6,7,7a-octahydro-1H-2-pyrindine;

4a-(3-hydroxyphenyl)-2-(2-methylphenoxymethyl)-2,3,4,4a,5,6,7,7a-octahydro-1H-2-pyrindinium succinate;

4a-(3-methoxyphenyl)-2-(3,5-dichlorobenzoylmethyl)-2,3,4,4a,5,6,7,7a-octahydro-1H-2-pyrindine;

4a-(3-ethoxyphenyl)-2-[3-(3-methyl-4-bromophenyl)-3-hydroxy]propyl-2,3,4,4a,5,6,7,7a-octahydro-1H-2-pyrindinium iodide;

4a-phenyl-2-[3-(2-ethyl-6-methylphenylthio)propyl]-2,3,4,4a,5,6,7,7a-octahydro-1H-2-pyrindinium perchlorate;

4a-(3-hydroxyphenyl)-2-[2-(3,4-dibromophenyl)-2-hydroxy]ethyl-2,3,4,4a,5,6,7,7a-octahydro-1H-2-pyrindine;

4a-phenyl-2-(3-phenylthio)propyl-2,3,4,4a,5,6,7,7a-octahydro-1H-2-pyrindinium citrate;

4a-phenyl-2-[3-(2-isopropylphenyl)propyl]-2,3,4,4a,5,6,7,7a-octahydro-1H-2-pyrindinium maleate;

4a-(3-ethoxyphenyl)-2-(2-phenyl-2-hydroxyethyl)-2,3,4,4a,5,6,7,7a-octahydro-1H-2-pyrindinium phosphate;

4a-phenyl-2-[2-(4-chlorophenyl)-2-hydroxyethyl]-2,3,4,4a,5,6,7,7a-octahydro-1H-2-pyrindinium methanesulfonate;

4a-(3-hydroxyphenyl)-2-[3-(2-chloro-3-bromophenyl)-3-hydroxypropyl]-2,3,4,4a,5,6,7,7a-octahydro-1H-2-pyrindine;

4a-(3-propoxyphenyl)-2-(2-ethylbenzoylethyl)-2,3,4,4a,5,6,7,7a-octahydro-1H-2-pyrindinium chloride;
4a-(3-ethoxyphenyl)-2-[3-(2-chlorophenylthio)-propyl]-2,3,4,4a,5,6,7,7a-octahydro-1H-2-pyrindine;
4a-phenyl-2-[3-(2-ethyl-5-bromophenyl)propyl]-2,3,4,4a,5,6,7,7a-octahydro-1H-2-pyrindine;
4a-(3-hydroxyphenyl)-2-[2-(3,5-diethylphenoxy)-ethyl]-2,3,4,4a,5,6,7,7a-octahydro-1H-2-pyrindinium stearate.
4a-phenyl-3-methyl-2-ethyl-2,3,4,4a,5,6,7,7a-octahydro-1H-2-pyrindine;
4a-phenyl-3-n-pentyl-2-methyl-2,3,4,4a,5,6,7,7a-octahydro-1H-2-pyrindine;
4a-phenyl-3-isobutyl-2-cyclopropylmethyl-2,3,4,4a,5,6,7,7a-octahydro-1H-2-pyrindine;
4a-(3-hydroxyphenyl)-3-ethyl-2-(3-chlorobenzyl)-2,3,4,4a,5,6,7,7a-octahydro-1H-2-pyrindine;
4a-(3-acetoxyphenyl)-3-methyl-2-(3-furylmethyl)-2,3,4,4a,5,6,7,7a-octahydro-1H-2-pyrindine;
4a-(3-ethoxyphenyl)-3-n-butyl-2-phenylthiomethyl-2,3,4,4a,5,6,7,7a-octahydro-1H-2-pyrindine;
4a-(3-isopropoxyphenyl)-3-methyl-2-(3,4-dimethyl-phenoxymethyl)-2,3,4,4a,5,6,7,7a-octahydro-1H-2-pyrindine;
4a-(3-methoxyphenyl)-3-n-propyl-2-benzyl-2,3,4,4a,5,6,7,7a-octahydro-1H-2-pyrindinium bromide;
4a-phenyl-3-methyl-2-n-propyl-2,3,4,4a,5,6,7,7a-octahydro-1H-2-pyrindinium chloride;
4a-phenyl-3-ethyl-2-n-octyl-2,3,4,4a,5,6,7,7a-octahydro-1H-2-pyrindinium oxalate;
4a-(3-ethoxyphenyl)-3-methyl-2-(3-ethylpentyl)-2,3,4,4a,5,6,7,7a-octahydro-1H-2-pyrindinium sulfate;
4a-(3-hydroxyphenyl)-3-ethyl-2-cyclopentylmethyl-2,3,4,4a,5,6,7,7a-octahydro-1H-2-pyrindinium phosphate;
4a-(3-formyloxyphenyl)-3-methyl-2-allyl-2,3,4,4a,5,6,7,7a-octahydro-1H-2-pyrindinium nitrate;
4a-(3-acetoxyphenyl)-3-ethyl-2-(3-pentenyl)-2,3,4,4a,5,6,7,7a-octahydro-1H-2-pyrindinium acetate; and the like.

It will be noted that the compounds provided by this invention which have the above general structural formula have two asymmetric centers, namely the 4a position and the 7a position. This invention comprehends both separated isomers and racemic mixtures of such isomers which are useful pharmacologically as analgesic agonist or antogonist drugs.

The above-described methods of preparation are believed to afford predominantly the 4a,7a-cis-octahydropyrindines of this invention. A preferred method for preparing the corresponding 4a,7a-trans isomers comprises catalytic hydrogenation of a 4a-aryl-hexahydropyrindine, specifically a pyrindine having a double bond at the 1,7a-position. Such hydrogenation generally is carried out by reacting a 4a-aryl-2-alkyl-3,4,4a,5,6,7-hexahydro-2-pyrindine with hydrogen in the presence of a catalyst such as platinum oxide. The hydrogenation typically is carried out in a solvent such as methanol or ethanol, and routinely is complete within about one to eight hours when carried out at about 25° C. under a hydrogen pressure of about 40 to about 80 p.s.i. The hydrogenation typically provide a mixture of the 1,7a-trans isomer and the 1,7a-cis isomer; however, the trans isomer generally predominates. Separation of the isomers can be readily effected by salt formation and crystallization. For example the racemic mixture of octahydropyrindines can be converted to a suitable salt such as the pirate or maleate salt, and the cis racemate normally crystallizes first from solvents such as diethyl ether and diisopropyl ether, and can accordingly be separated from the trans by filtration. The trans racemate then can be recovered from the filtrate and purified by recrystallization.

The preparation of the 4a-aryl-octahydropyrindines provided by this invention requires starting materials, many of which are hitherto unknown and not readily available. For example, the above-described preferred method for preparing trans-4a-aryl-2-substituted-octahydro-1H-2-pyrindines requires the corresponding 4a-aryl-2-substituted-3,4,4a,5,6,7-hexahydro-2-pyrindines, ie. $\Delta^{1,7a}$-hexahydropyrindines. Such compounds can be prepared by condensing phenyl lithium or a 3-substituted phenyl lithium with a 1-alkyl-4-piperidone to provide the corresponding 1-alkyl-4-phenyl or substituted phenyl-4-hydroxypiperidine. Dehydration of the 4-hydroxypiperidine derivative affords a 1-alkyl-4-aryl-1,2,3,6-tetrahydropyrindine. The tetrahydropyrindine derivative next is reacted with a propylene dihalide such as 3-chloropropylbromide to afford a 1-alkyl-4-aryl-4-(3-halopropyl)-1,2,3,4-tetrahydropyridine, which is then readily cyclized by reaction with sodium iodide in acetonitrile to provide the corresponding 4a-aryl-2-alkyl-3,4,4a,5,6,7-hexahydro-2-pyrindine.

The 3-unsubstituted pyrindines of the invention; ie. compounds having the above formula when R is hydrogen, utilize 4a-aryl-tetrahydro-2,6-dioxocyclopenta[c]-pyrans as starting materials, while the 3-alkyl pyrindines, ie. compounds having the above formula when R is $C_1$-$C_5$ alkyl, require a 2-aryl-2-alkenyl-1-aminomethylcyclopentane derivative. Both such starting materials are prepared from 2-arylcyclohexanones such as 2-phenylcyclohexanone and 2-(3-methoxyphenyl)cyclohexanone. For the preparation of the dioxocyclopentapyran derivatives, the 2-arylcyclohexanone is alkylated at the 2-position by reaction with an alkyl haloacetate such as ethyl chloroacetate, in the presence of a base such as sodium hydride, thereby providing the corresponding 2-aryl-2-alkoxycarbonylmethylcyclohexanone. Similarly, in the preparation of 2-aryl-2-alkenyl-1-aminomethylcyclopentanes, a 2-arylcyclohexanone is first alkylated at the 2-position by reaction with an alkenyl halide, such as allyl iodide or 2-butenyl bromide, in the presence of a base such as sodium hydride, to provide the corresponding 2-aryl-2-alkenylcyclohexanone. Both the 2-aryl-2-alkoxycarbonylmethylcyclohexanones and the 2-aryl-2-alkenylcyclohexanones are next formylated at the 6 position by reaction with an alkyl formate such as ethyl formate in the presence of metallic sodium or potassium. The formyl cyclohexanone derivatives are next reacted with para-toluene sulfonyl azide, thus effecting displacement of the 6-formyl moiety with a diazo group to provide, respectively, 2-aryl-2-alkoxycarbonylmethyl-6-diazocyclohexanones and 2-aryl-2-alkenyl-6-diazocyclohexanones. Such diazocyclohexanone derivatives are next photolyzed with a light having a wavelength of about 3000 angstroms in an alcoholic solvent such as methanol to effect ring contraction with concomitant expulsion of nitrogen gas to provide, respectively, 2-aryl-2-alkoxycarbonylmethyl-1-methoxycarbonylcyclopentanes and 2-aryl-2-alkenyl-1-methoxycarbonylcyclopentanes. Such compounds are next de-esterified, ie. hydrolyzed, by reaction with aqueous alkali to provide the corresponding diacid and mono-acid. Specifically, hydrolysis of a 2-aryl-2-alkoxycarbonylmethyl-1-methoxycarbonylcyclopentane provides the corresponding 2-aryl-2-hydroxycarbonylmethyl-1-hydroxycarbonylcyclopentane. Similarly, hydrolysis of a 2-aryl-2-alkenyl-1-methoxycarbonylcyclopentane affords the corresponding 2-aryl-2-alkenyl-1-hydroxycarbonylcyclopentane. The diacid, namely the 2-aryl-2-hydroxycarbonylmethyl-1-hydroxycarbonylcyclopentane, is next cyclized by reaction with an acid halide such as acetyl chloride to provide the corresponding anhydride, a 4a-aryl-tetrahydro-2,6-dioxocyclopenta[c]pyran. These pyrans are the starting materials for the preparation of the 3-unsubstituted pyrindines of this invention.

The mono-acid, namely the 2-aryl-2-alkenyl-1-hydroxycarbonylcyclopentane, is next converted to an acid halide by reaction with a halogenating agent such as thionyl chloride. The acid halide so formed is then reacted with an amine, for instance ammonia or a primary amine such as methylamine or benzylamine, thus providing the corresponding amide, namely a 2-aryl-2-alkenyl-1-aminocarbonylcyclopentane. Such amide is then reduced, for example by reaction with lithium aluminum hydride or the like, to provide the corresponding 2-aryl-2-alkenyl-1-aminomethylcyclopentane derivative, which compound is the starting material for preparing the 3-alkyl pyridine derivatives of this invention, as set forth hereinabove.

Certain of the 4a-aryl-2-substituted octahydro-1H-2-pyrindines of this invention have found utility in the treatment of pain, and accordingly can be used to effect analgesia in a subject suffering from pain and in need of treatment. Additionally, the pyrindine derivatives of this invention have been found to possess both analgesic agonist and analgesic antagonist properties, and as such are capable of producing analgesia in a mammal which at the same time, because of the analgesic antagonist activity, having a greatly decreased incidence of addiction liability. Such ability of the compounds disclosed herein to cause analgesic agonist as well as analgesic antagonist effects in mammals is thus responsible for a decrease in any addictive properties of a particular drug caused by its opiate-like analgesic action. The compounds are thus particularly valuable since they produce analgesia with only minimal physical dependance liability. Certain of the compounds are additionally useful in combating the undesirable effects produced by opiates such as morphine.

The analgesic activity possessed by the compounds of this invention has been determined by testing such compounds in standard animal assays routinely used to measure analgesic action attributable to test compounds. Such assays include the mouse-writhing test and the rat tail jerk assay.

As indicated hereinbefore, the compounds of this invention have demonstrated analgesic activity when tested in the standard mouse writhing assay. In this procedure, writhing is induced in mice by the intraperitoneal injection of acetic acid. The degree of analgesic activity possessed by a drug is then determined by observing the inhibition of such writhing when the drug is administered prior to the administration of the acetic acid. When 4a-(3-methoxyphenyl)-2-methyl-2,3,4,4a,5,6,7,7a-octahydro-1H-2-pyridine, as the hydrochloride salt, is administered subcutaneously at the rate of 20 mg/kg of body weight to a mouse in which writhing has been induced, there is observed a 100 percent reduction in such writhing. A subcutaneous dose of 10 mg/kg. produces a 96 percent inhibition of writhing. Similarly, an oral dose of the above-named compound produces a 100 percent inhibition of writhing at a dose of 20 mg/kg., and a 98 percent inhibition at a dose of 10 mg/kg. Additionally, naloxone was found to totally prevent the inhibitory action of the compound at an subcutaneous dose of 5 mg./kg., thus indicating that the compound is an opiate-type analgesic. When tested in the rat tail jerk assay, the above-named compound produced a significant increase in reaction time at dose levels of 80 mg./kg., both subcutaneously and orally, and produced the same effect at oral doses as low as 20 mg./kg., all measurements being made at ½ hour and 2 hours following dosing.

Similarly tested was 4a-(3-hydroxyphenyl)-2-methyl-2,3,4,4a,5,6,7,7a-octahydro-1H-2-pyrindine. At a subcutaneous dose of 0.5 mg/kg, the compound caused a 75 percent inhibition of writhing in a test animal. With an oral dose of 10 mg./kg. of such compound, a 98 percent inhibition of writhing was observed after ½ hour following dosing. Naloxone totally prevented the inhibitory action of the compound at a 0.5 mg/kg subcutaneous dose. The rat tail jerk assay revealed that the compound caused a significant increase in reaction time at subcutaneous and oral doses of 20 mg./kg.

4a-Phenyl-2-methyl-2,3,4,4a,5,6,7,7a-octahydro-1H-2-pyrindinium bromide, another compound of this invention, effected a 70 percent inhibition of writhing in a group of test animals at a dose of 100 mg./kg., ½ hour following dosing. At an oral dose of 20 mg/kg, the compound caused a 58 percent inhibition after 1½ hours following dosing, which effect was completely prevented in the presence of naloxone. The rat tail assay indicated that the compound caused only a moderate increase in reaction time at dose levels of 80 mg/kg.

The 4a-aryl-2-substituted-2,3,4,4a,5,6,7,7a-octahydro-1H-2-pyrindines provided by this invention are thus useful in producing analgesia in mammals such as humans. Such compounds can be administered to a mammal by either the oral or the parenteral route. It generally is preferred to utilize a pharmaceutically acceptable acid addition salt of the pyrindine derivative when the dosage is by the oral route, since such salts are easily formulated for convenient oral administration. For example, one or more pharmacologically active compounds of this invention, either as the free base or as a pharmaceutically acceptable acid addition salt, will be formulated for oral administration by admixing such compounds with any of a number of commonly used diluents, excipients, carriers or the like. Examples of such diluents and excipients commonly employed in pharmaceutical preparations include starch powder, sucrose, cellulose, magnesium stearate, lactose, calcium sulfate, sodium benzoate and related diluents. Such compositions can be molded into tablets or enclosed in telescoping gelatin capsules for convenient administration. If desired, the active compounds of this invention can additionally be combined with one or more other agents known to effect analgesia, such as caffeine, acetaminophen, propoxyphene, and the like.

The active compounds of this invention can additionally be formulated as sterile aqueous or non-aqueous solutions, suspensions, and emulsions for convenient parenteral administration. Non-aqueous vehicles commonly utilized in such formulations include propylene glycol, vegetable oils such as olive oil, as well as various organic esters such as ethyl oleate. Useful aqueous solutions for oral and parenteral administration include isotonic saline solution.

The precise dosage of active ingredient, that is the amount of one or more of the pharmacologically active 4a-aryl-2-substituted-octahydro-1H-2-pyrindines of this invention adminstered to a mammal, such as a human subject for example, may be varied over a relatively wide range, it being necessary that the formulations should constitute a proportion of one or more of the active ingredients of this invention such that a suitable dosage will be obtained. Such suitable dosage will depend on the particular therapeutic effect desired, on the particular route of administration being utilized, and on the duration of treatment, as well as the precise condition being treated. Typically the dosages of the active compounds of this invention will range from about 1.0 to about 25 mg./kg. of animal body weight per day, appropriately divided for administration from 1 to 4 times per day. Preferred oral dosages will generally range from about 2 to about 50 mg./kg.

In order to demonstrate more fully the operation of this invention, the following examples are provided by way of illustration.

EXAMPLE 1

2-Phenyl-2-ethoxycarbonylmethyl-6-formylcyclohexanone

A solution of 130 g. of 2-phenyl-2-ethoxycarbonylmethylcyclohexanone in 2000 ml. of diethyl ether containing 56 g. of ethyl formate and 11.5 g. of metallic sodium was stirred at 25° C. for forty-eight hours. The reaction mixture was then added to 1000 ml. of ice-water, and the ethereal layer was removed. The aqueous layer was acidified to pH 6.5 by the addition of 1 N hydrochloric acid, and further extracted with fresh diethyl ether. The ethereal extracts were combined, washed with water, and dried. Evaporation of the solvent under reduced pressure provided 98 g. of 2-phenyl-2-ethoxycarbonylmethyl-6-formylcyclohexanone as an oil. B.P. 158°–175° C. at 0.5 torr.

Analysis Calc. for $C_{17}H_{20}O_4$: Theory: C, 70.81; H, 6.99. Found: C, 70.85; H, 6.77.

EXAMPLE 2

Following the procedure set forth in Example 1, 2-(3-methoxyphenyl)-2-ethoxycarbonylmethylcyclohexanone was reacted with ethyl formate in the presence of metallic sodium to provide 2-(3-methoxyphenyl)-2-ethoxycarbonylmethyl-6-formylcyclohexanone.

EXAMPLE 3

2-Phenyl-2-(2-propenyl)cyclohexanone

A solution of 87.0 g. of 2-phenylcyclohexanone in 100 ml. of benzene was added dropwise over 1 hour to a stirred refluxing solution of 28.0 g. of sodium amide in 400 ml. of benzene. The reaction mixture was heated at reflux for an additional 2.5 hours, and then cooled to 0° C. in an ice bath. To the cold reaction mixture was added in one portion of a solution of 83.5 g. of allyl iodide in 100 ml. of benzene. The reaction mixture was heated at reflux for ½ hour, and then cooled to 25° C. and poured onto 400 g. of ice. The organic benzene layer was separated, washed with water and dried. Evaporation of the solvent afforded 50 g. of 2-phenyl-2-(2-propenyl)cyclohexanone. B.P. 114°–120° C. at 0.1 torr.

EXAMPLE 4

2-Phenyl-2-(2-propenyl)-6-formylcyclohexanone

A solution of 30 g. of 2-phenyl-2-(2-propenyl)cyclohexanone in 600 ml. of diethyl ether containing 3.4 g. of sodium metal and 11.8 g. of ethyl formate was stirred at 25° C. for forty-eight hours. The reaction mixture was then added to water, and the organic layer was separated and set aside. The aqueous layer was acidified to pH 2.5 by the addition of aqueous hydrochloric acid. The aqueous acid layer was extracted with fresh diethyl ether. The ethereal extracts were combined, washed with water, dried, and the solvent was removed therefrom by evaporation under reduced pressure to provide the product as an oil. The oil so formed was distilled to afford 14.6 g. of 2-phenyl-2-(2-propenyl)-6-formylcyclohexanone. B.P. 125°–130° C. at 0.1 torr.

EXAMPLE 5

2-Phenyl-2-ethoxycarbonylmethyl-6-diazocyclohexanone

A solution of 50.0 g. of 2-phenyl-2-ethoxycarbonylmethyl-6-formylcyclohexanone in 500 ml. of diethyl ether was stirred at 25° C. while a solution of 24.8 g. of diethylamine in 100 ml. of diethyl ether was added dropwise over thirty minutes. After stirring the reaction mixture for two hours at 25° C., the solution was cooled to 5° C., and then a solution of 33.5 g. of p-toluenesulfonylazide in 50 ml. of diethyl ether was added dropwise over fifteen minutes. The reaction mixture was allowed to warm to room temperature, and was stirred for an additional five hours. The reaction mixture was then washed with water and dried. Evaporation of the solvent under reduced pressure afforded 43.0 g. of 2-phenyl-2-ethoxycarbonylmethyl-6-diazocyclohexanone as an oil. IR (neet) 2080 cm$^{-1}$ diazo group.

EXAMPLES 6–7

Following the procedure set forth in Example 5, 2-(3-methoxyphenyl)-2-ethoxycarbonylmethyl-6-formylcyclohexanone was converted to 2-(3-methoxyphenyl)-2-ethoxycarbonylmethyl-6-diazocyclohexanone, and 2-phenyl-2-(2-propenyl)-6-formylcyclohexanone was converted to 2-phenyl-2-(2-propenyl)-6-diazocyclohexanone.

EXAMPLE 8

2-Phenyl-2-ethoxycarbonylmethyl-1-methoxycarbonylcyclopentane

A solution of 57 g. of 2-phenyl-2-ethoxycarbonylmethyl-6-diazocyclohexanone in 500 ml. of anhydrous methanol was stirred at 25° C. while nitrogen gas was bubbled through the reaction mixture. The solution was photolyzed for forty hours with a quartz lamp having wavelength of 3000 A. The solvent was then removed under reduced pressure to provide the product as a crude oil, which was dissolved in 500 ml. of diethyl ether. The ethereal solution was washed with aqueous sodium bicarbonate solution, with water, and dried. Removal of the solvent under reduced pressure afforded 27.4 g. of 2-phenyl-2-ethoxycarbonylmethyl-1-methoxycarbonylcyclopentane as an oil. The oil was further purified by distillation. B.P. 160°–190° C. at 0.02 torr.

Analysis Calc. for $C_{17}H_{22}O_4$: Theory: C, 70.32; H, 7.64. Found: C, 70.30; H, 7.36.

EXAMPLE 9-10

Following the procedure set forth in Example 8, 2-(3-methoxyphenyl)-2-ethoxycarbonylmethyl-6-diazocyclohexanone was photolyzed at 3000 A to provide 2-(3-methoxyphenyl)-2-ethoxycarbonylmethyl-1-methoxycarbonylcyclopentane. B.P. 190°–210° C.

Analysis Calc. for $C_{18}H_{24}O_5$: Theory: C, 67.48; H, 7.55. Found: C, 67.61; H, 7.37.

Similarly, 2-phenyl-2-(2-propenyl)-6-diazocyclohexanone was irradiated with ultraviolet light at 3000 A from a quartz lamp in the presence of methanol to provide 2-phenyl-2-(2-propenyl)-1-methoxycarbonylcyclopentane. B.P. 113°–115° C. at 0.1 torr.

Analysis Calc. for $C_{16}H_{20}O_2$: Theory: C, 78.65; H, 8.25. Found: C, 78.80; H, 7.99.

Analysis Calc. for $C_{19}H_{25}O_5$: Theory: C, 68.24; H, 7.84. Found: C, 68.15; H, 7.57.

EXAMPLE 11

2-(3-Methoxyphenyl)-2-hydroxycarbonylmethyl-1-hydroxycarbonylcyclopentane

A solution of 2-(3-methoxyphenyl)-2-ethoxycarbonylmethyl-1-methoxycarbonylcyclopentane in 650 ml. of 1,4-dioxane containing 500 ml. of 5 percent aqueous potassium hydroxide was stirred and heated at reflux for twelve hours. After cooling the reaction mixture to room temperature, 500 ml. of water was added. The reaction mixture was made acidic by the addition of 2 N hydrochloric acid, and the aqueous acidic mixture was extracted several times with equal volumes of diethyl ether. The ethereal extracts were combined, washed with water, and dried. Evaporation of the solvent under reduced pressure provided 38 g. of 2-(3-methoxyphenyl)-2-hydroxycarbonylmethyl-1-hydroxycarbonylcyclopentane as a crystalline solid. M.P. 175°–180° C.

EXAMPLES 12-13

Following the procedure set forth in Example 11, 2-phenyl-2-ethoxycarbonylmethyl-1-methoxycarbonylcyclopentane was hydrolyzed to provide 2-phenyl-2-hydroxycarbonylmethyl-1-hydroxycarbonylcyclopentane. M.P. 205°–208° C.

Analysis Calc. for $C_{14}H_{16}O_4$: Theory: C, 67.73; H, 6.50. Found: C, 67.70; H, 6.32.

2-Phenyl-2-(2-propenyl)-1-methoxycarbonylcyclopentane was hydrolyzed by reaction with aqueous potassium hydroxide to provide 2-phenyl-2-(2-propenyl)-1-hydroxycarbonylcyclopentane.

EXAMPLE 14

Tetrahydro-4-phenyl-2,6-dioxocyclopenta[c]pyran

A solution of 25 g. of 2-phenyl-2-hydroxycarbonylmethyl-1-hydroxycarbonylcyclopentane in 150 ml. of acetyl chloride was stirred and heated at reflux for four hours. After cooling the reaction mixture to room temperature, the excess solvent was removed by evaporation under reduced pressure, providing 26 g. of tetrahydro-4-phenyl-2,6-dioxocyclopenta[c]pyran as an oil. The product was further purified by distillation. B.P. 205°–207° C. at 0.25 torr.

Analysis Calc. for $C_{14}H_{15}O_3$: Theory: C, 73.03; H, 6.13. Found: C, 73.30; H, 6.37.

EXAMPLE 15

Following the procedure set forth in Example 14, 2-(3-methoxyphenyl)-2-hydroxycarbonyl-1-hydroxycarbonylcyclopentane was dehydrated and cyclized by reaction with acetyl chloride to provide tetrahydro-4-(3-methoxyphenyl)-2,6-dioxocyclopenta[c]pyran. B.P. 200°–220° C.

EXAMPLE 16

2-Phenyl-2-(2-propenyl)-1-chlorocarbonylcyclopentane

To a stirred solution of 6.2 g. of 2-phenyl-2-(2-propenyl)-1-hydroxycarbonylcyclopentane in 100 ml. of chloroform was added dropwise over thirty minutes 30 g. of thionyl chloride. The reaction mixture was then heated at reflux and stirred for fifteen hours. After cooling the reaction mixture, the solvent was removed therefrom by evaporation under reduced pressure to afford 7.4 g. of 2-phenyl-2-(2-propenyl)-1-chlorocarbonylcyclopentane.

EXAMPLE 17

4a-(3-Methoxyphenyl)-2-benzyl-2,3,4,4a,5,6,7,7a-octahydro-1,3-dioxo-1H-2-pyrindine.

A solution of 10.7 g. of benzylamine in 100 ml. of toluene was stirred at 25° C. while a solution of tetrahydro-4-(3-methoxyphenyl)-2,6-dioxocyclopenta[c]pyran in 300 ml. of toluene was added dropwise over one hour. Following complete addition of the pyran derivative, the reaction mixture was stirred and heated at reflux for three days in a flask equipped with a Dean-Stark trap for water removal. Following the reflux period, the reaction mixture was cooled to room temperature and the solvent was removed by evaporation under reduced pressure, thus providing the product as a crude oil. The oil was dissolved in 400 ml. of 1 N sodium hydroxide solution and the alkaline reaction mixture was heated to 50° C. for fifteen minutes. The aqueous alkaline mixture was then extracted with diethyl ether, and the ethereal extracts were combined, washed with water, dried, and the solvent was evaporated therefrom under reduced pressure to provide the product as a solid residue. Recrystallization of the solid from diethyl ether afforded 4a-(3-methoxyphenyl)-2-benzyl-2,3,4,4a,5,6,7,7a-octahydro-1,3-dioxo-1H-2-pyrindine. M.P. 75°–77° C.

Analysis Calc. for $C_{22}H_{23}NO_3$: Theory: C, 75.62; H, 6.63; N, 4.01. Found: C, 75.40; H, 6.58; N, 3.78.

EXAMPLE 18

Tetrahydro-4-phenyl-2,6-dioxocyclopenta[c]pyran was reacted with benzylamine according to the procedure of Example 17 to provide 4a-phenyl-2-benzyl-2,3,4,4a,5,6,7,7a-octahydro-1,3-dioxo-1H-2-pyrindine. M.P. 77°–79° C.

Analysis Calc. for $C_{21}H_{21}NO_2$: Theory: C, 78.97; H, 6.63; N, 4.39. Found: C, 78.73; H, 6.65; N, 4.26.

EXAMPLE 19

4a-Phenyl-2-benzyl-2,3,4,4a,5,6,7,7a-octahydro-1H-2-pyrindine

A solution of 18 g. of 4a-phenyl-2-benzyl-2,3,4,4a,5,6,7,7a-octahydro-1,3-dioxo-1H-2-pyrindine dissolved in 200 ml. of tetrahydrofuran was added dropwise over ninety minutes to a stirred suspension of 5.8 g. of lithium aluminum hydride in 150 ml. of tetrahydrofuran. After the addition was complete, the reaction mixture was heated at reflux for ten hours. While maintaining the temperature of the reaction mixture below 50°

C., 50 ml. of ethyl acetate was added dropwise over fifteen minutes, followed by the addition of 100 ml. of aqueous ammonium chloride. Additional tetrahydrofuran was then added to the aqueous reaction mixture to effect separation of the organic layer from the aqueous layer. The organic layer was decanted and concentrated under reduced pressure to provide the product as an oil. The oil thus prepared was dissolved in 500 ml. of diethyl ether. The ethereal solution was washed with water, dried, and the solvent was removed by evaporation under reduced pressure to provide 15 g. of 4a-phenyl-2-benzyl-2,3,4,4a,5,6,7,7a-octahydro-1H-2-pyrindine.

EXAMPLE 20

Following the procedure set forth in Example 19, 4a-(3-methoxyphenyl)-2-benzyl-2,3,4,4a,5,6,7,7a-octahydro-1,3-dioxo-1H-2-pyrindine was reduced by reaction with lithium aluminum hydride to provide 4a-(3-methoxyphenyl)-2-benzyl-2,3,4,4a,5,6,7,7a-octahydro-1H-2-pyrindine.

EXAMPLE 21

4a-Phenyl-2,3,4,4a,5,6,7,7a-octahydro-1H-2-pyrindine

A solution of 21 g. of 4a-phenyl-2-benzyl-2,3,4,4a,5,6,7,7a-octahydro-1H-2-pyrindine in 172 ml. of ethanol was stirred while 7 g. of 5 percent palladium suspended on carbon was added in one portion. The reaction mixture was stirred under a hydrogen gas atmosphere at 60 psi and heated at 60° C. for three hours. The reaction mixture was cooled to room temperature, filtered, and the solvent was removed by evaporation under reduced pressure to provide 13.3 g. of the product as an oil. The oil was distilled to afford 4a-phenyl-2,3,4,4a,5,6,7,7a-octahydro-1H-2-pyrindine.

EXAMPLE 22

4a-(3-Methoxyphenyl)-2-benzyl-2,3,4,4a,5,6,7,7a-octahydro-1H-2-pyrindine was hydrogenated in the presence of palladium suspended on charcoal according to the procedure set forth in Example 21 to provide 4a-(3-methoxyphenyl)-2,3,4,4a,5,6,7,7a-octahydro-1H-2-pyrindine. B.P. 145°-160° C., 0.05 torr.

EXAMPLE 23

4a-(3-Hydroxyphenyl)-2,3,4,4a,5,6,7,7a-octahydro-1H-2-pyrindine

A solution of 8.4 g. of 4a-(3-methoxyphenyl)-2,3,4,4a,5,6,7,7a-octahydro-1H-2-pyrindine dissolved in 60 ml. of glacial acetic acid and 60 ml. of 48 percent aqueous hydrobromine and was stirred and heated at reflux for fifteen hours. After cooling the reaction mixture to room temperature, the reaction mixture was added to 100 g. of ice, and the pH of the resulting aqueous solution was adjusted to 10.2 by the addition of concentrated aqueous sodium hydroxide solution. The alkaline reaction mixture was then extracted with 400 ml. of a mixture of 3 parts n-butanol and 1 part benzene. The extract was separated, washed several times with water, dried, and the solvent was removed by evaporation under reduced pressure to provide the product as a crude solid. The solid so formed was crystallized from ethyl acetate to afford 4.2 g. of 4a-(3-hydroxyphenyl)-2,3,4,4a,5,6,7,7a-octahydro-1H-2-pyrindine. M.P. 180°-181° C.

Analysis Calc. for $C_{14}H_{19}NO$: Theory: C, 77.38; H, 8.81; N, 6.45. Found: C, 77.56; H, 8.84; N, 6.24.

EXAMPLE 24

4a-Phenyl-2-(2-propenyl)-2,3,4,4a,5,6,7,7a-octahydro-1H-2-pyrindine

A solution of 2 g. of 4a-phenyl-2,3,4,4a,5,6,7,7a-octahydro-1H-2-pyrindine in 30 ml. of N,N-dimethylformamide containing 1.23 g. of sodium bicarbonate was stirred at 25° C. while 1.23 g. of 2-propenyl bromide was added in one portion. The reaction mixture was stirred and heated at reflux for four hours. After being cooled to room temperature, the reaction mixture was filtered and concentrated to an oil under reduced pressure. The residual oil was dissolved in 300 ml. of diethyl ether. The ethereal solution was washed with water, dried, and the solvent was then removed by evaporation under reduced pressure, thus providing 4a-phenyl-2-(2-propenyl)-2,3,4,4a,5,6,7,7a-octahydro-1H-2-pyrindine as an oil. The oil so formed was dissolved in 150 ml. of fresh diethyl ether, and hydrogen bromide gas was bubbled through the ethereal solution. The precipitated salt was collected by filtration and recrystallized from diisopropyl ether and isopropanol to afford 1.3 g. of 4a-phenyl-2-(2-propenyl)-2,3,4,4a,5,6,7,7a-octahydro-1H-2-pyrindinium bromide. M.P. 185°-187° C.

Analysis Calc. for $C_{17}H_{24}BrN$: Theory: C, 63.36; H, 7.51; N, 4.35. Found: C, 63.63; H, 7.24; N, 4.24.

EXAMPLES 25-26

Following the procedure set forth in Example 24, the following 1-alkyl pyridine derivatives were prepared by reaction of 4a-phenyl-2,3,4,4a,5,6,7,7a-octahydro-1H-2-pyrindine with an appropriate alkylating agent.

4a-Phenyl-2-n-propyl-2,3,4,4a,5,6,7,7a-octahydro-1H-2-pyrindinium bromide. M.P. 245°-247° C.

Analysis Calc. for $C_{17}H_{26}BrN$: Theory: C, 62.96; H, 8.08; N, 4.32. Found: C, 62.74; H, 8.22; N, 4.23.

4a-Phenyl-2-n-pentyl-2,3,4,4a,5,6,7,7a-octahydro-1H-2-pyrindinium bromide. M.P. 240°-243° C.

Analysis Calc. for $C_{19}H_{30}BrN$: Theory: C, 64.77; H, 8.58; N, 3.98. Found: C, 65.04; H, 8.70; N, 3.87.

EXAMPLE 27

4a-Phenyl-2-methyl-2,3,4,4a,5,6,7,7a-octahydro-1H-2-pyrindinium bromide

A solution of 3.0 g. of 4a-phenyl-2,3,4,4a,5,6,7,7a-octahydro-1H-2-pyrindine in 10 ml. of 88% formic acid was stirred at 20° C. while 10 ml. of 38% formaldehyde was added dropwise over fifteen minutes. The reaction mixture was then heated at 95° C. for eight hours. After cooling the reaction mixture to 25° C. 100 ml. of 4 N hydrochloric acid was added dropwise over thirty minutes. The aqueous acidic reaction mixture was concentrated under reduced pressure to provide an oily residue. The oil was then dissolved in 100 ml. of water, and the aqueous solution was made basic by the addition of 50 percent aqueous sodium hydroxide solution. The product precipitated out of the aqueous alkaline solution, and was extracted into diethyl ether. The ethereal extracts were combined, washed with water, dried, and the solvent was evaporated under reduced pressure to provide 4a-phenyl-2-methyl-2,3,4,4a,5,6,7,7a-octahydro-1H-2-pyrindine as an oil. The oil so formed was dissolved in 150 ml. of diethyl ether. The ethereal solution was stirred at 25° C. while a solution of 10 ml. of 48 percent hydrobromic acid in 10 ml. of ethanol was added dropwise over ten minutes. The product precipitated out of solution and was recovered by filtration. The solid precipitate was recrystallized from diisopropyl ether and isopropanol to afford 2.7 g. of 4a-phenyl-2-methyl-2,3,4,4a,5,6,7,7a-octahydro-1H-2-pyrindinium bromide. M.P. 209°–210° C.

Analysis Calc. for $C_{15}H_{22}BrN$: Theory: C, 60.81; H, 7.49; N, 4.73. Found: C, 60.55; H, 7.49; N, 4.57.

EXAMPLE 28

4a-Phenyl-2-(2-phenylethyl)-2,3,4,4a,5,6,7,7a-octahydro-1H-2-pyrindinium bromide To a cold solution (0°–5° C.) of 3.0 g. of 4a-phenyl-2,3,4,4a,5,6,7,7a-octahydro-1H-2-pyrindine in 47 ml. of methanol containing 14 ml. of water and 2.6 g. of potassium carbonate was added 2.6 g. of phenylacetyl chloride in one portion. The reaction mixture was stirred at 0°–5° C. for thirty minutes and then was warmed to 25° C., at which it was stirred for an additional one hour. The reaction mixture was concentrated under reduced pressure, leaving an oily residue. The oil was then dissolved in 500 ml. of diethyl ether and washed with dilute aqueous sodium bicarbonate solution and with water. After drying the ethereal solution, the solvent was evaporated under reduced pressure to afford 4a-phenyl-2-phenylacetyl-2,3,4,4a,5,6,7,7a-octahydro-1H-2-pyridine formed in the above acylation reaction as an oil.

The oil so formed was dissolved in 25 ml. of tetrahydrofuran and added dropwise over thirty minutes to a stirred suspension of 3.0 g. of lithium aluminum hydride in 150 ml. of tetrahydrofuran. After the addition was complete, the reaction mixture was stirred and heated at reflux for four hours. After the reaction mixture was cooled to 30° C., 60 ml. of ethyl acetate was added, followed by the addition to the reaction mixture of 100 ml. of saturated aqueous ammonium tartrate solution. The organic layer was separated by decanting, and the aqueous layer was extracted with diethyl ether. The organic solvents were combined and concentrated under reduced pressure to provide the product as a crude oil. The oil was then dissolved in 400 ml. of diethyl ether, washed with water, and dried. Removal of the solvent by evaporation under reduced pressure provided 4a-phenyl-2-(2-phenylethyl)-2,3,4,4a,5,6,7,7a-octahydro-1H-2-pyrindine as an oil. The oil was then dissolved in 150 ml. of diethyl ether and added to a solution of 10 ml. of 48 percent hydrobromic acid in 10 ml. of ethanol. The hydrobromide salt of the above-named pyrindine precipitated out of solution and was recrystallized from diisopropyl ether and isopropanol to provide 2.4 g. of 4a-phenyl-2-(2-phenylethyl)-2,3,4,4a,5,6,7,7a-octahydro-1H-2-pyrindinium bromide. M.P. 269°–270° C.

Analysis Calc. for $C_{22}H_{28}BrN$: Theory: C, 68.39; H, 7.30; N, 3.63. Found: C, 68.61; H, 7.57; N, 3.69.

EXAMPLE 29

Following the procedure outlined in Example 28, 4a-phenyl-2,3,4,4a,5,6,7,7a-octahydro-1H-2-pyrindine was acylated with cyclopropanecarboxylic acid chloride to provide 4a-phenyl-2-cyclopropanecarbonyl-2,3,4,4a,5,6,7,7a-octahydro-1H-2-pyrindine. Reduction of the acylated pyrindine intermediate by reaction with lithium aluminium hydride afforded the corresponding 2-alkyl pyrindine, which when reacted with hydrobromic acid provided 4a-phenyl-2-cyclopropylmethyl-2,3,4,4a,5,6,7,7a-octahydro-1H-2-pyrindinium bromide. M.P. 240°–241° C.

Analysis Calc. for $C_{18}H_{26}BrN$: Theory: C, 64.28; H, 7.79; N, 4.16. Found: C, 64.54; H, 7.51; N, 4.13.

EXAMPLE 30

4a-(3-Methoxyphenyl)-2-methyl-2,3,4,4a,5,6,7,7a-octahydro-1,3-dioxo-1H-2-pyrindine A solution of 75 ml. of toluene containing 1.76 ml. of liquid methylamine was cooled to −70° C. in a dry ice/acetone bath and stirred while a solution of 10.4 g. of tetrahydro-4-(3-methoxyphenyl)-2,6-dioxocyclopenta[c]pyran in 125 ml. of toluene was added dropwise over thirty minutes. The reaction mixture was warmed to room temperature and then heated at reflux for twenty-two hours. The reaction mixture was again cooled to room temperature and concentrated under reduced pressure to an oil. The oil so formed was dissolved in 152 ml. of 1 N sodium hydroxide solution and was heated with stirring to 50° C. for fifteen minutes. The product was extracted from the aqueous alkaline reaction mixture into diethyl ether. The ethereal extracts were combined, washed with water, and dried. Evaporation of the solvent under reduced pressure provided 8.3 g. of 4a-(3-methoxyphenyl)-2-methyl-2,3,4,4a,5,6,7,7a-octahydro-1,3-dioxo-1H-2-pyrindine.

EXAMPLE 31

4a-(3-Methoxyphenyl)-2-methyl-2,3,4,4a,5,6,7,7a-octahydro-1H-2-pyrindine

Reduction of 8.2 g. of 4a-(3-methoxyphenyl)-2-methyl-2,3,4,4a,5,6,7,7a-octahydro-1,3-dioxo-1H-2-pyrindine from Example 30 by reaction with lithium aluminum hydride according to the procedure set forth in Example 19 provided 4.6 g. of 4a-(3-methoxyphenyl)-2-methyl-2,3,4,4a,5,6,7,7a-octahydro-1H-2-pyrindine. B.P. 133°–138° C. at 0.25 torr.

Analysis Calc. for $C_{16}H_{23}NO$: Theory: C, 78.32; H, 9.45; N, 5.71. Found: C, 78.13; H, 9.30; N, 5.68.

EXAMPLE 32

A solution of 4a-(3-methoxyphenyl)-2-methyl-2,3,4,4a,5,6,7,7a-octahydro-1H-2-pyrindine in 100 ml. of diethyl ether was stirred while hydrogen chloride gas was bubbled through the solution. The reaction mixture was stirred for thirty minutes and then filtered. The solid product was recrystallized from diisopropyl ether and isopropanol to provide 4a-(3-methoxyphenyl)-2-methyl-2,3,4,4a,5,6,7,7a-octahydro-1H-2-pyrindinium chloride. M.P. 175°–177° C.

Analysis Calc. for $C_{16}H_{24}HOCl$: Theory: C, 68.19; H, 8.58; N, 4.97. Found: C, 68.00; H, 8.22; N, 4.68.

EXAMPLE 33

4a-(3-Hydroxyphenyl)-2-methyl-2,3,4,4a,5,6,7,7a-octahydro-1H-2-pyrindine

A solution of 1.6 g. of 4a-(3-methoxyphenyl)-2-methyl-2,3,4,4a,5,6,7,7a-octahydro-1H-2-pyrindine in 12 ml. of acetic acid containing 12 ml. of 48 percent hydrobromic acid was stirred and heated at reflux for fifteen hours. The acidic reaction mixture was cooled to about 10° C. and the pH was adjusted to 10.2 by the addition of 50 percent aqueous sodium hydroxide solution. The product was insoluble in the aqueous alkaline solution and was extracted therefrom into a solution of 90 ml. of n-butanol and 30 ml. of benzene. The organic solution was then separated, washed with water and dried. Evaporation of the excess solvent under reduced pressure provided the de-methylated product as an oil, which was then crystallized from diethyl ether and ethyl acetate to provide 4a-(3-hydroxyphenyl)-2-methyl-2,3,4,4a,5,6,7,7a-octahydro-1H-2-pyrindine. M.P. 151°–153° C.

Analysis Calc. for $C_{15}H_{21}NO$: Theory: C, 77.88; H, 9.15; N, 6.05. Found: C, 77.60; H, 8.88; N, 5.76.

EXAMPLE 34

4a-(3-Hydroxyphenyl)-2-(2-phenylethyl)-2,3,4,4a,5,6,7,7a-octahydro-1H-2-pyrindinium bromide A solution of 2.17 g. of 4a-(3-hydroxyphenyl)-2,3,4,4a,5,6,7,7a-octahydro-1H-2-pyrindine prepared as described in Example 23 in 50 ml. of N,N-dimethylformamide containing 3.95 g. of triethylamine was stirred at room temperature while 3.87 g. of phenylacetyl chloride was added dropwise over 15 minutes. Following complete addition, the reaction mixture was heated at 70° C. for two hours, and then poured into 200 ml. of water. The aqueous reaction mixture was extracted several times with diethyl ether, and the ethereal extracts were combined, washed with saturated aqueous sodium chloride solution and with water, and dried. Removal of the solvent by evaporation under reduced pressure afforded 4a-(3-hydroxyphenyl)-2-(2-phenylacetyl)-2,3,4,4a,-5,6,7,7a-octahydro-1H-2-pyrindine. Such product was dissolved in 50 ml. of tetrahydrofuran and stirred while a solution of 4.0 g. of lithium aluminum hydride in 150 ml. of tetrahydrofuran was added dropwise over thirty minutes. The reaction mixture was then heated at reflux for four hours, and then cooled to about 25° C. While the reaction mixture was stirred, 25 ml. of ethyl acetate was added, followed by the addition of a saturated aqueous solution of ammonium tartrate. The reaction mixture was then filtered and the filtrate was concentrated by evaporation of the solvent under reduced pressure. The product thus formed was dissolved in diethyl ether and washed with water and dried. Removal of the solvent then provided 4a-(3-hydroxyphenyl)-2-(2-

EXAMPLE 36

4a-(3-Hydroxyphenyl)-2-(2-tetrahydrofurylmethyl)-2,3,4,4a,-5,6,7,7a-octahydro-1H-2-pyrindinium bromide A solution of 1.5 g. of 4a-(3-hydroxyphenyl)-2,3,4,4a,5,6,7,7a-octahydro-1H-2-pyrindine in 15 ml. of N,N-dimethylformamide containing 1.0 g. of sodium bicarbonate and 0.95 g. of 2-tetrahydrofurylmethyl bromide was heated at reflux for four hours. After cooling the reaction mixture to about 25° C., the mixture was extracted several times with diethyl ether. The ethereal extracts were combined, washed with water, and dried. Removal of the solvent by evaporation under reduced pressure provided 4a-(3-hydroxyphenyl)-2-(2-tetrahydrofurylmethyl)-2,3,4,4a,5,6,7,7a-octahydro-1H-2-pyrindine as an oil. The oil so formed was dissolved in diethyl ether and added to a solution of hydrogen bromide gas in diethyl ether. The product crystallized out of solution and was collected by filtration to provide 1.0 g. of 4a-(3-hydroxyphenyl)-2-(2-tetrahydrofurylmethyl)-2,3,4,4a,5,6,7,7a-octahydro-1H-2-pyrindinium bromide. M.P. 190°–192° C.

Analysis Calc. for $C_{19}H_{28}NO_2Br$: Theory: C, 59.69; H, 7.38; N, 3.66. Found: C, 59.89; H, 7.40; N, 3.78.

EXAMPLES 37–39

Following the procedure set forth in Example 36, 4a-(3-hydroxyphenyl)-2,3,4,4a,5,6,7,7a-octahydro-1H-2-pyrindine was reacted with allyl iodide in the presence of sodium bicarbonate to provide 4a-(3-hydroxyphenyl)-2-(2-propenyl)-2,3,4,4a,5,6,7,7a-octahydro-1H-2-pyrindine. M.P. 106°–108° C.

Analysis Calc. for $C_{17}H_{23}NO$: Theory: C, 79.33; H, 9.01; N, 5.44. Found: C, 79.29; H, 8.92; N, 5.44.

Similarly 4a-(3-methoxyphenyl)-2,3,4,4a,5,6,7,7a-octahydro-1H-2-pyrindine from Example 22 was reacted with 1-iodopropane in the presence of sodium bicarbonate to provide 4a-(3a-methoxyphenyl)-2-n-propyl-2,3,4,4a,5,6,7,7a-octahydro-1H-2-pyrindine, which was then converted to the hydrobromide salt by reaction with hydrogen bromide gas in diethyl ether. M.P. 197°–199° C.

Analysis Calc. for $C_{18}H_{28}NOBr$: Theory: C, 61.02; H, 7.97; N, 3.95. Found: C, 60.65; H, 7.52; N, 4.07.

Similarly, 4a-(2-methoxyphenyl)-2,3,4,4a,5,6,7,7a-octahydro-1H-2-pyrindine was reacted with 1-bromopentane in the presence of sodium bicarbonate to provide 4-(3-methoxyphenyl)-2-n-pentyl-2,3,4,4a,5,6,7,7a-octahydro-1H-2-pyrindine. Such compound was treated with hydrogen bromide gas in diethyl ether to provide 4a-(3-methoxyphenyl)-2-n-pentyl-2,3,4,4a,5,6,7,7a-octahydro-1H-2-pyrindinium bromide as a crystalline solid. M.P. 179°–181° C.

Analysis Calc. for $C_{20}H_{32}NOBr$: Theory: C, 62.82; H, 8.44; N, 4.18. Found: C, 62.87; H, 7.98; N, 4.02.

EXAMPLE 40

4a-(3-Hydroxyphenyl)-2-n-propyl-2,3,4,4a,5,6,7,7a-octahydro-1H-2-pyrindinium bromide A solution of 2.0 g. of 4a-(3-methoxyphenyl)-2-n-propyl-2,3,4,4a,5,6,7,7a-octahydro-1H-2-pyrindine, prepared as described in Example 38, dissolved in 20 ml. of glacial acetic acid and 20 ml. of 48 percent aqueous hydrobromic acid was stirred and heated at reflux for twelve hours. The reaction mixture was then cooled and poured over 100 g. of ice, and the resulting aqueous solution was made alkaline by the addition of aqueous sodium hydroxide to pH 10.2. The aqueous alkaline mixture was extracted with 200 ml. of a mixture of 3 parts n-butanol and 1 part benzene. The extracts were combined, washed with water and dried. Removal of the solvent by evaporation under reduced pressure provided 1.3 g. of 4a-(3-hydroxyphenyl)-2-n-propyl-2,3,4,4a,5,6,7,7a-octahydro-1H-2-pyrindine is an oil. The oil was dissolved in diethyl ether and added to a solution of hydrogen bromide gas in diethyl ether. The hydrobromide salt of the above-named compound crystallized and was recovered by filtration to give 1.1 g. of 4a-(3-hydroxyphenyl)-2-n-propyl-2,3,4,4a,5,6,7,7a-octahydro-1H-2-pyrindinium bromide. M.P. 235°–236° C.

Analysis Calc. for $C_{15}H_{26}NOBr$: Theory: C, 60.00; H, 7.70; N, 4.12. Found: C, 59.98; H, 7.50; N, 3.98.

EXAMPLE 41

Following the procedure set forth in Example 40, 4a-(3-methoxyphenyl)-2-n-pentyl-2,3,4,4a,5,6,7,7a-octahydro-1H-2-pyrindine was reacted with aqueous hydrobromic acid in glacial acetic acid to afford 4a-(3-hydroxyphenyl)-2-n-pentyl-2,3,4,4a,5,6,7,7a-octahydro- 1H-2-pyrindine, which was then converted to the corresponding hydrogen bromide salt. M.P. 171°–173° C.

Analysis Calc. for $C_{20}H_{30}NOBr$: Theory: C, 61.95; H, 8.21; N, 3.80. Found: C, 61.65; H, 7.93; N, 3.54.

EXAMPLE 42

2-Phenyl-2-(2-propenyl)-1-(N-methyl)aminocarbonylcyclopentane

A solution of 2 ml. of methylamine in 40 ml. of toluene was stirred at −40° C. while a solution of 7.3 g. of 2-phenyl-2-(2-propenyl)-1-chlorocarbonylcyclopentane, from Example 16, in 100 ml. of toluene was added dropwise over fifteen minutes. The reaction mixture was warmed to 25° C. and stirred for an additional one hour. The reaction mixture was then concentrated to an oil by evaporation of the solvent, and the oil was dissolved in 50 ml. of 1 N sodium hydroxide solution. The alkaline mixture was extracted several times with diethyl ether, and the ethereal extracts were combined, washed with water, and dried, and the solvent was removed therefrom by evaporation under reduced pressure to afford 6.9 g. of 2-phenyl-2-(2-propenyl)-1-(N-methyl)aminocarbonylcyclopentane.

EXAMPLE 43

2-Phenyl-2-(2-propenyl)-1-N-methylaminomethylcyclopentane

A solution of 190 ml. of a seventy percent solution of sodium bis(2-methoxyethoxy)aluminum hydride in benzene was cooled to 10° C. and stirred while a solution of 63 g. of 2-phenyl-2-(2-propenyl)-1-N-methylaminocarbonylcyclopentane, from Example 42, in 575 ml. of benzene was added dropwise over one hour. The reaction mixture was then warmed to 25° C. and stirred for five hours. The reaction mixture was again cooled to 10° C. and made acidic by the addition of 200 ml. of ten percent aqueous hydrochloric acid. The organic layer was separated, and the aqueous acid layer was made alkaline by the addition of concentrated sodium hydroxide solution. The product was insoluble in the aqueous alkaline solution, and was extracted therefrom into diethyl ether. The ethereal extracts were combined, washed with water, and dried. Removal of the solvent by evaporation under reduced pressure provided 30.3 g. of 2-phenyl-2-(2-propenyl)-1-N-methylaminomethylcyclopentane. B.P. 122°–125° C. at 0.1 torr.

Analysis Calc. for $C_{16}H_{23}N$: Theory: C, 83.79; H, 10.11; N, 6.11. Found: C, 83.57; H, 9.84; N, 6.07.

EXAMPLE 44

2,3-Dimethyl-4a-phenyl-2,3,4,4a,5,6,7,7a-octahydro-1H-2-pyrindine

To a stirred solution of 2.54 g. of mercuric chloride in 20 ml. of tetrahydrofuran was added dropwise over fifteen minutes a solution of 4.0 g. of 2-phenyl-2-(2-propenyl)-1-N-methylaminomethylcyclopentane in 30 ml. of tetrahydrofuran. The reaction mixture was stirred for fifteen minutes at room temperature, and then a solution of 0.25 g. of sodium borohydride in 2.5 ml. of 2.5 N sodium hydroxide solution was added dropwise over five minutes. Following complete addition, the reaction mixture was stirred for an additional fifteen minutes and then decanted, and the solvent was removed therefrom by evaporation under reduced pressure to provide 2,3-dimethyl-4a-phenyl-2,3,4,4a,5,6,7,7a-octahydro-1H-2-pyrindine as an oil. The oil so formed was dissolved in diethyl ether, and hydrogen chloride gas was bubbled through the solution, thereby precipitating the hydrochloride salt of the above named pyridine derivative. The salt so formed was recrystallized from 30 ml. of diisopropyl ether and 6 ml. of isopropyl alcohol, providing 2,3-dimethyl-4a-phenyl-2,3,4,4a,5,6,7,7a-octahydro-1H-2-pyrindinium chloride. M.P. 189°–191° C.

Analysis Calc. for $C_{16}H_{24}NCl$: Theory: C, 72.29; H, 9.10; N, 5.27. Found: C, 72.31; H, 8.92; N, 5.26.

EXAMPLE 45

1-Methyl-4-hydroxy-4-(3-methoxyphenyl)piperidine

A solution of 159 ml. of n-butyllithium in 100 ml. of hexane containing 47.7 g. of 3-methoxybromobenzene was stirred at −25° C. for twenty minutes and then was warmed to room temperature and stirred for one hour to provide 3-methoxyphenyl lithium. The reaction mixture was chilled to 10° C. and stirred while a solution of 50 g. of 1-methyl-4-piperidone in 100 ml. of diethyl ether was added dropwise over thirty minutes. Following complete addition, the reaction mixture was stirred for two hours, and then was diluted with 50 ml. of saturated aqueous sodium chloride solution. The solution was extracted several times with diethyl ether, and the ethereal extracts were combined and concentrated to dryness to provide 38 g. of 1-methyl-4-hydroxy-4-(3-methoxyphenyl)piperidine.

EXAMPLE 46

1-Methyl-4-(3-methoxyphenyl)-1,2,3,6-tetrahydropyridine

To a stirred solution of 200 ml. of 50 g. of phosphorous pentoxide in methanesulfonic acid was added portionwise over four minutes 59 g. of 1-methyl-4-hydroxy-4-(3-hydroxyphenyl)piperidine. The reaction was exothermic and the temperature rose to 70° C. After complete addition of the piperidine derivative, the reaction mixture was added to 200 g. of ice, and the aqueous mixture was made alkaline by the addition of ammonium hydroxide. The alkaline mixture was extracted several times with diethyl ether, and the ethereal extracts were combined, washed with water, dried, and the solvent was removed by evaporation under reduced pressure to provide 44.7 g. of the product as an oil. The oil thus formed was distilled to provide 1-methyl-4-(3-methoxyphenyl)-1,2,3,6-tetrahydropyridine, B.P. 123°–138° C. at 0.1 torr.

Analysis Calc. for $C_{13}H_{17}NO$: Theory: C, 76.81; H, 8.43; N, 6.89. Found: C, 76.52; H, 8.15; N, 6.67.

EXAMPLE 47

4a-Phenyl-2-methyl-3,4,4a,5,6,7-hexahydro-2-pyrindine

To a stirred cold (−5° to −10° C.) solution of 25 g. of 1-methyl-4-phenyl-1,2,3,6-tetrahydropyridine in 450 ml. of tetrahydrofuran was added dropwise over thirty minutes 90 ml. of 1.6 molar n-butyl lithium in hexane. Following complete addition, the solution was stirred for ten minutes at −10° C. and then cooled to −30° C. The cold solution next was added dropwise over twenty minutes to a stirred solution of 73.3 g. of 3-chloropropylbromide in 300 ml. of diethyl ether chilled to −50° C. Following complete addition, the reaction mixture was warmed to −20° C. and diluted with 500 ml. of saturated aqueous sodium chloride that had been chilled to 0° C. The organic layer was separated, washed with water, and the product was extracted therefrom into 1200 ml. of 1 N hydrochloric acid. The aqueous acid layer was washed with diethyl ether and then was made alkaline by the dropwise addition of concentrated aqueous sodium hydroxide. The alkaline solution was extracted several times with diethyl ether, and the ethereal extracts were combined, washed with water and dried. Evaporation of the solvent at 10° C. afforded an oil which was dissolved in 2500 ml. of acetonitrile containing 52.5 g. of sodium iodide. The reaction mixture was heated at reflux and stirred for twenty-four hours, after which time the solvent was removed by evaporation under reduced pressure. The crude product thus formed was dissolved in a mixture of 800 ml. of 1 N sodium hydroxide and 1000 ml. of diethyl ether, and the mixture was stirred vigorously for forty-five minutes. The ethereal layer then was separated, washed with saturated aqueous sodium chloride and dried. Removal of the solvent by evaporation under reduced pressure afforded the product as an oil, which upon distillation provided 21.5 g. of 4a-phenyl-2-methyl-3,4,4a,5,6,7-hexahydro-2-pyrindine. B.P. 110°–112° C. at 0.075 torr.

Analysis Calc. for $C_{15}H_{19}N$: Theory: C, 84.46; H, 8.98; N, 6.57. Found: C, 84.74; H, 8.72; N, 6.28.

EXAMPLE 48

Following the procedure set out in Example 47, 1-methyl-4-(3-methoxyphenyl)-1,2,3,6-tetrahydropyridine was reacted with 3-chloropropylbromide and sodium iodide to afford 4a-(3-methoxyphenyl)-2-methyl-3,4,4a,5,6,7-hexahydro-2-pyrindine. B.P. 132°–134° C. at 0.1 torr.

Analysis Calc. for $C_{16}H_{22}NO$: Theory: C, 78.97; H, 8.70; N, 5.76. Found: C, 76.58; H, 8.28; N, 5.36.

m/e: theory 243; found 243.

EXAMPLE 49 trans-4a-Phenyl-2-methyl-2,3,4,4a,5,6,7,7a-octahydro-1H-2-pyrindine

A solution of 5.0 g. of 4a-phenyl-1-methyl-3,4,4a,5,6,7-hexahydro-2-pyrindine in 50 ml. of ethanol containing 500 mg of platinum oxide was stirred at room temperature for four hours under a hydrogen atmosphere of 60 p.s.i. The mixture then was filtered and the solvent was removed from the filtrate by evaporation to provide an oil which was shown by NMR and high pressure liquid chromatography to consist of about forty percent cis-4a-phenyl-1-methyl-2,3,4,4a,5,6,7,7a-octahydro-1H-2-pyrindine and about sixty percent of the corresponding trans isomer. The mixture was dissolved in 50 ml. of diethyl ether and made acidic by the addition of a saturated solution of hydrogen bromide dissolved in diethyl ether. Concentration of the ethereal solution effected crystallization. The mixture was filtered and the precipitate was recrystallized from 30 ml. of isopropanol and 70 ml. of diisopropyl ether to afford 2.6 g. of cis-4a-phenyl-2-methyl-2,3,4,4a,5,6,7,7a-octahydro-1H-2-pyrindinium bromide.

The filtrate was evaporated to dryness and the residue was dissolved in water. The aqueous solution was made alkaline by the addition of 1 N sodium hydroxide, and the aqueous alkaline solution was extracted with diethyl ether. The ethereal extracts were combined, washed with water and dried. Removal of the solvent by evaporation under reduced pressure afforded 2.57 g. of trans-4a-phenyl-2-methyl-2,3,4,4a,5,6,7,7a-octahydro-1H-2-pyrindine.

The trans-pyrindine derivative was dissolved in 120 ml. of ethanol and reacted with 2.76 g. of picric acid to provide 2.7 g. of trans-4a-phenyl-2-methyl-2,3,4,4a,5,6,7,7a-octahydro-1H-2-pyrindinium picrate. M.P. 167°–168° C.

Analysis Calc. for $C_{21}H_{24}N_4O_7$: Theory: C, 56.75; H, 5.44; N, 12.61. Found: C, 56.99; H, 5.65; N, 12.46.

EXAMPLE 50

The preparation described in Example 49 was repeated except that the trans-pyrindine derivative was reacted with maleic acid and isolated as trans-4a-phenyl-2-methyl-2,3,4,4a,5,6,7,7a-octahydro-1H-2-pyrindinium maleate. M.P. 113°–114° C.

Analysis Calc. for $C_{19}H_{25}NO_4$: Theory: C, 68.86; H, 7.60; N, 4.23. Found: C, 68.66; H, 7.82; N, 3.98.

EXAMPLE 51

Following the procedure set forth in Example 49, 4a-(3-methoxyphenyl)-2-methyl-3,4,4a5,6,7-hexahydro-2-pyrindine was hydrogenated over platinum oxide to provide a 60:40 mixture of trans-4a-(3-methoxyphenyl)-2-methyl-2,3,4,4a,5,6,7,7a-octahydro-1H-2-pyrindine and the corresponding cis-isomer. The trans isomer was crystallized as the picrate salt. The cis isomer was isolated as the free base, namely cis-4a-(3-methoxyphenyl)-2-methyl-2,3,4,4a,5,6,7,7a-octahydro-1H-2-pyrindine. M.P. 40°–43° C.

Analysis Calc. for $C_{16}H_{23}NO$: Theory: C, 78.32; H, 9.45; N, 5.71. Found: C, 78.26; H, 9.31; N, 5.61.

EXAMPLE 52 trans-4a-(3-Hydroxyphenyl)-2-methyl-2,3,4,4a,5,6,7,7a-octahydro-1H-2-pyrindine

A solution of 3.5 g. of trans-4a-(3-methoxyphenyl)-2-methyl-2,3,4,4a,5,6,7,7a-octahydro-1H-2-pyrindine in 35 ml. of glacial acetic acid containing 35 ml. of fifty percent aqueous hydrobromic acid was stirred and heated at reflux for fifteen hours. The reaction mixture then was cooled to room temperature and diluted with 100 ml. of ice-water. The aqueous acid solution was made basic by the addition of concentrated sodium hydroxide to pH 9.8, and the aqueous alkaline solution was extracted several times with diethyl ether. The ethereal extracts were combined, washed with water and dried. Removal of the solvent by evaporation under reduced pressure afforded 1.8 g. of the product as a solid. The solid so formed was recrystallized from 150 ml. of ethyl acetate to provide 1.65 g. of trans-4a-(3-hydroxyphenyl)-2-methyl-2,3,4,4a,5,6,7,7a-octahydro-1H-2-pyrindine. M.P. 192°–194° C.

Analysis Calc. for $C_{15}H_{21}NO$: Theory: C, 77.88; H, 9.15; N, 6.05. Found: C, 77.48; H, 8.71; N, 5.67.

I claim:

1. A compound having the formula

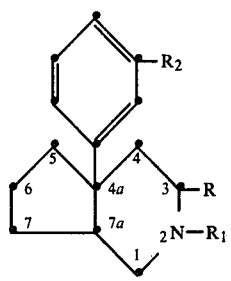

wherein:
R is hydrogen or $C_1$-$C_5$ alkyl;
$R_1$ is

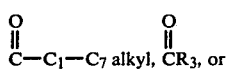

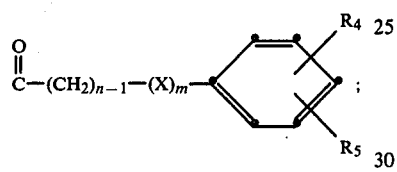

in which
$R_3$ is $C_2$-$C_7$ alkenyl, $C_3$-$C_6$ cycloalkyl, furyl, or tetrahydrofuryl;
$R_4$ and $R_5$ independently are hydrogen, $C_1$-$C_3$ alkyl, or halogen;
n is 1, 2, or 3;
m is 0 or 1, except that when m is 0, n is other than 0;
X is CO, CHOH, CH=CH, S, or O, except that when n is 0, X is other than S or O;
$R_2$ is hydrogen, hydroxy, $C_1$-$C_3$ alkoxy, or $C_1$-$C_3$ alkanoyloxy; or
a non-toxic pharmaceutically acceptable acid addition salt thereof.

2. A compound having a formula

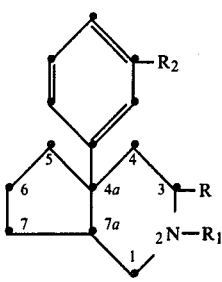

wherein:
R is hydrogen;
$R_1$ is $CH_2R_3$,
in which $R_3$ is $C_2$-$C_7$ alkenyl;
$R_2$ is hydrogen, hydroxy, $C_1$-$C_3$ alkoxy, or $C_1$-$C_3$ alkanoyloxy; or
a non-toxic pharmaceutically acceptable acid addition salt thereof.

3. The compound of claim 2, said compound being 4a-(3-hydroxyphenyl)-2-(2-propenyl)-2,3,4,4a,5,6,7,7a-octahydro-1H-2-pyrindine.

4. A compound having the formula

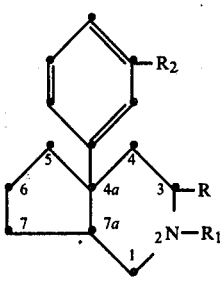

wherein:
R is hydrogen;
$R_1$ is $CH_2R_3$,
in which $R_3$ is tetrahydrofuryl;
$R_2$ is hydrogen, hydroxy, $C_1$-$C_3$ alkoxy, or $C_1$-$C_3$ alkanoyloxy; or
a non-toxic pharmaceutically acceptable acid addition salt thereof.

5. The compound of claim 4, said compound being 4a-(3-hydroxyphenyl)-2-(2-tetrahydrofurylmethyl)-2,3,4,4a,5,6,7,7a-octahydro-1H-2-pyrindine.

* * * * *